US011793803B2

(12) United States Patent
Park et al.

(10) Patent No.: US 11,793,803 B2
(45) Date of Patent: *Oct. 24, 2023

(54) PARTICLE AND PHARMACEUTICAL COMPOSITION COMPRISING AN INSOLUBLE CAMPTOTHECIN COMPOUND WITH DOUBLE CORE-SHELL STRUCTURE AND METHOD FOR MANUFACTURING THE SAME

(71) Applicant: SN BIOSCIENCE INC., Seongnam-si (KR)

(72) Inventors: Young Hwan Park, Wonju-si (KR); Il Hyun Lee, Incheon (KR)

(73) Assignee: SN BIOSCIENCE INC., Seongnam-si (KR)

( * ) Notice: Subject to any disclaimer, the term of this patent is extended or adjusted under 35 U.S.C. 154(b) by 232 days.

This patent is subject to a terminal disclaimer.

(21) Appl. No.: 17/233,040

(22) Filed: Apr. 16, 2021

(65) Prior Publication Data

US 2021/0228568 A1  Jul. 29, 2021

Related U.S. Application Data

(62) Division of application No. 16/015,470, filed on Jun. 22, 2018, now Pat. No. 10,980,796.

(30) Foreign Application Priority Data

Jun. 22, 2017 (KR) .................. 10-2017-0079354

(51) Int. Cl.
*A61K 31/4745* (2006.01)
*A61P 35/00* (2006.01)
(Continued)

(52) U.S. Cl.
CPC ........ *A61K 31/4745* (2013.01); *A61K 9/1075* (2013.01); *A61K 9/19* (2013.01);
(Continued)

(58) Field of Classification Search
CPC .................................. A61K 31/4745
See application file for complete search history.

(56) References Cited

U.S. PATENT DOCUMENTS 10,980,796 B2    4/2021 Park et al.
2002/0193391 A1* 12/2002 Bouscarel ............ A61K 9/0019
                                                      514/283
(Continued)

FOREIGN PATENT DOCUMENTS

CN     101199857      6/2008
CN     101628919 A    1/2010
(Continued)

OTHER PUBLICATIONS

CAS Registry Record for Camptothecin (CAS# 7689-03-4). Entered STN Nov. 16, 1984, 30 printed pages. (Year: 1984).*
(Continued)

*Primary Examiner* — Isaac Shomer
(74) *Attorney, Agent, or Firm* — Sughrue Mion, PLLC

(57) ABSTRACT

A drug delivery system having an inner core-shell like structure containing a poorly soluble camptothecin compound and a water-soluble camptothecin compound, and an outer amphiphilic polymer shell surrounding the inner core-shell like structure, a manufacturing method therefor, and uses of the drug delivery system in treating cancer are disclosed. The core-shell structured particles form very stable particles and show a mono-distribution of particles before and after freeze-drying. The particles show excellent results compared with existing particles which do not con-
(Continued)

tain the inner core-shell like structure, in animal efficacy tests and pharmacokinetic tests.

17 Claims, 9 Drawing Sheets

(51) Int. Cl.
  *A61K 9/50* (2006.01)
  *A61K 9/107* (2006.01)
  *A61K 9/19* (2006.01)
(52) U.S. Cl.
  CPC .......... *A61K 9/5031* (2013.01); *A61K 9/5089* (2013.01); *A61P 35/00* (2018.01); *Y10S 977/773* (2013.01); *Y10S 977/906* (2013.01)

(56) References Cited

U.S. PATENT DOCUMENTS

| | | | |
|---|---|---|---|
| 2009/0061010 | A1* | 3/2009 | Zale .................... C07C 275/16 424/501 |
| 2010/0068285 | A1 | 3/2010 | Zale et al. |
| 2010/0203150 | A1 | 8/2010 | Lee et al. |
| 2010/0216804 | A1 | 8/2010 | Zale et al. |
| 2010/0247654 | A1 | 9/2010 | Hsiue et al. |
| 2012/0100220 | A1 | 4/2012 | Hsu et al. |
| 2014/0128421 | A1 | 5/2014 | Lv et al. |
| 2014/0314864 | A1 | 10/2014 | Cheng et al. |
| 2015/0265716 | A1 | 9/2015 | Valencia et al. |

FOREIGN PATENT DOCUMENTS

| | | |
|---|---|---|
| CN | 101869712 A | 10/2010 |
| CN | 102961332 A | 3/2013 |
| CN | 103638027 A | 3/2014 |
| CN | 106661138 A | 5/2017 |
| JP | 2007-512373 A | 5/2007 |
| JP | 2014514278 A | 4/2013 |
| KR | 19990069033 | 9/1999 |
| KR | 10-2001-0105239 A | 11/2001 |
| KR | 10-2002-0096585 A | 12/2002 |
| KR | 10-2010-0076862 A | 7/2010 |
| WO | 2006/049447 A1 | 5/2006 |
| WO | 2014/059022 A | 4/2014 |
| WO | 2016009227 | 1/2016 |

OTHER PUBLICATIONS

CAS Registry Record for SN-38 (CAS# 86639-52-3). Entered STN Nov. 16, 1984, 16 printed pages. (Year: 1984).*
CAS Registry Record for 1-hydroxycamptothecin (CAS# 19685-09-7). Entered STN Nov. 16, 1984, 18 printed pages. (Year: 1984).*
Hu Shiqi, "Study on preparation of novel nano-formulation of poorly soluble drug by using Amphiphilic drugs", Doctoral Dissertation of Zhejiang University, Jun. 12, 2017 (63 pages total) (Year: 2017).*
Kulthe et al., "Polymeric micelles: authoritative aspects for drug delivery", Designed Monomers and Polymers, vol. 15, No. 5, Sep. 2012, pp. 465-521 (58 pages total).
Opanasopit et al., "Block Copolymer Design for Camptothecin Incorporation into Polymeric Micelles for Passive Tumor Targeting", Pharmaceutical Research, vol. 21, No. 11, Nov. 2004 (8 pages total).
International Search Report (ISR) and Written Opinion of the International Searching Authority from corresponding PCT Application No. PCT/KR2018/007114, dated Nov. 2, 2018.
Clinton F. Stewart et al., "Disposition of irinotecan and SN-38 following oral and intravenous irinotecan dosing in mice", Cancer Chemother Pharmacol, 1997, vol. 40, pp. 259-265.
Office Action from corresponding Korean Paten Application No. 10-2018-0072357 dated Oct. 7, 2019.
R Kunii, H Onishi, K-i Ueki, K-i Koyama, Y Machida. "Particle Characteristics and Biodistribution of Camptothecin-Loaded PLA/(PEG-PPG-PEG) Nanoparticles." Drug Delivery, vol. 15, 2008, pp. 3-10. (Year: 2008).
K Derakhshandeh, M Soheili, S Dadashzadeh, R Saghiri. "Preparation and in vitro characterization of 9-nitrocamptothecin-loaded long circulating nanoparticles for delivery in cancer patients." International Journal of Nanomedicine, vol. 5, 2010, pp. 463-471. (Year: 2010).
D Schmid et al. "Nanoencapsulation of ABT-737 and camptothecin enhances their clinical potential through synergistic antitumor effects and reduction of systemic toxicity." Cell Death and Disease, vol. 5, e1454, 2014, pp. 1-11. (Year: 2014).
JB Cannon. "Lipids in Transdermal and Topical Drug Delivery." American Pharmaceutical Review, published Dec. 1, 2014, pp. 1-9. Downloaded from https://www.americanpharmaceuticalreview.com/Featured-Articles/170872-Lipids-in-Transdermal-and-Topical-Drug-Delivery/on Nov. 7, 2019. (Year: 2014).
Khan Academy. "Structure of the plasma membrane." Downloaded from https://www.khanacademy.org/science/high-school-biology/hs-cells/hs-the-cell-membrane/a/structure-of-the-plasma-membrane on Nov. 7, 2019, printed pp. 1-19. (Year: 2019).
K Kataoka, A Harada, Y Nagasaki. "Block copolymer micelles for drug delivery: Design, characterization and biological significance." Advanced Drug Delivery Reviews, vol. 64, 2012, pp. 37-48. (Year: 2012).
Caselaw Access Project. "In re Legator, 53 C.C.P.A. 729, 352 F.2d 377; 147 U.S.P.Q. 322 (1965)." https://cite.case.law/ccpa/53/729/ accessed Feb. 18, 2020, originally published Nov. 10, 1965, 5 printed pages. (Year: 1965).
ScienceDirect. "Micelle." https://www.sciencedirect.com/topics/medicine-and-dentistry/micelle accessed Apr. 29, 2020, pp. 1-11. (Year: 2020).
Google Translate. English Translation of CN-101199857-A. https://patents.google.com/patent/CN101199857A/en?oq=PLA-PEG-PLA+camptothecin accessed Jun. 26, 2020, originally published in Chinese in 2008, pp. 1-6. (Year: 2008).
Wassim Abdelwahed, Ghania Degobert, Serge Stainmesse, Hatem Fessi. "Freeze-drying of nanoparticles: Formulation, process and storage considerations." Advanced Drug Delivery Reviews 58 (2006) 1688-1713. (Year: 2006).
Jakob Beirowski et al. "Freeze-Drying of Nanosuspensions, 1: Freezing Rate Versus Formulation Design as Critical Factors to Preserve the Original Particle Size Distribution." Journal of Pharmaceutical Sciences, vol. 100, No. 5, May 2011, pp. 1958-1968. (Year: 2011).
Hu Shiqi, "Study on preparation of novel nano-formulation of poorly soluble drug by using Amphiphilic drugs", Doctoral Dissertation of Zhejiang University, Jun. 12, 2017 (63 pages total).
Communication dated May 7, 2021 from the China National Intellectual Property Administration in CN Application No. 201880041446.5.
Communication dated Apr. 28, 2022 from the Patent Office of Israel in IL Application No. 270818.
Office Action dated Apr. 13, 2023 in U.S. Appl. No. 17/233,153.
Office Action dated Mar. 21, 2023 in U.S. Appl. No. 17/233,069.
C. E. Mora-Huertas et al., "Polymer-based nanocapsules for drug delivery" International Journal of Pharmaceutics, 2010, vol. 385, pp. 113-142 (30 pages total).
Office Action dated Apr. 7, 2023 in U.S. Appl. No. 17/233,091.

* cited by examiner

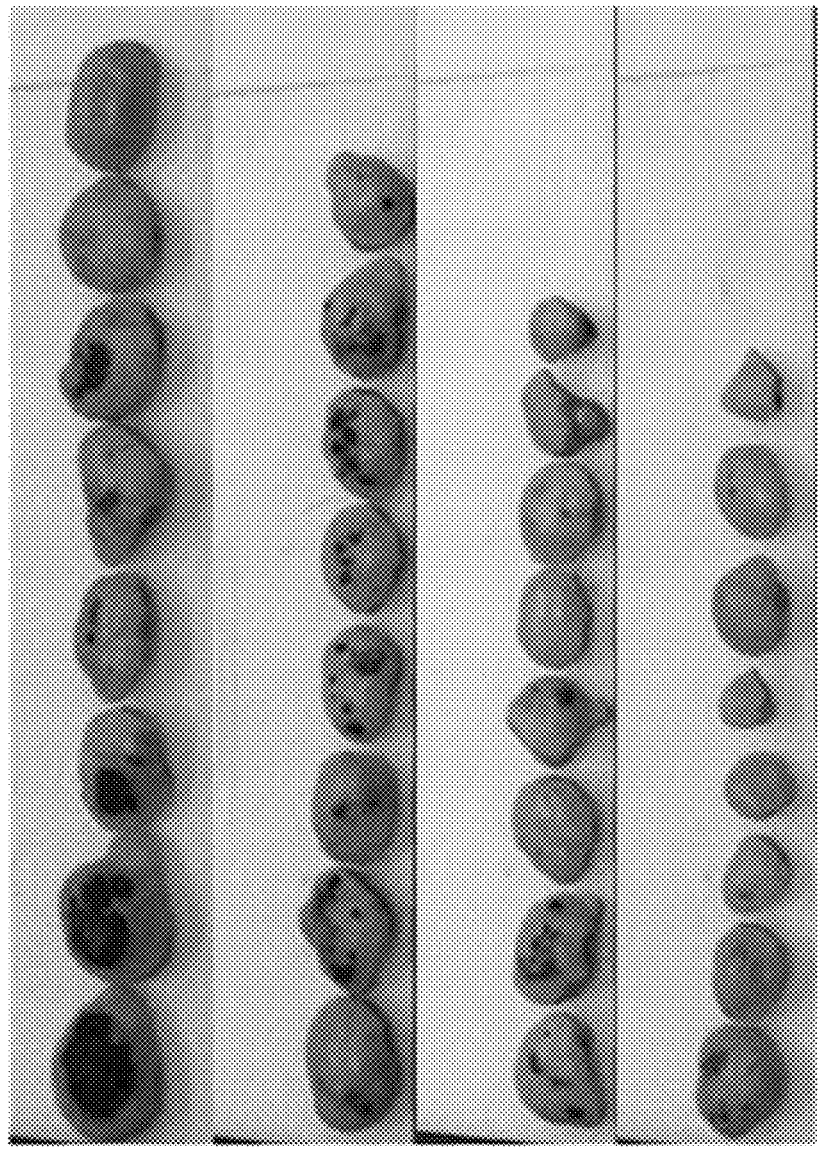

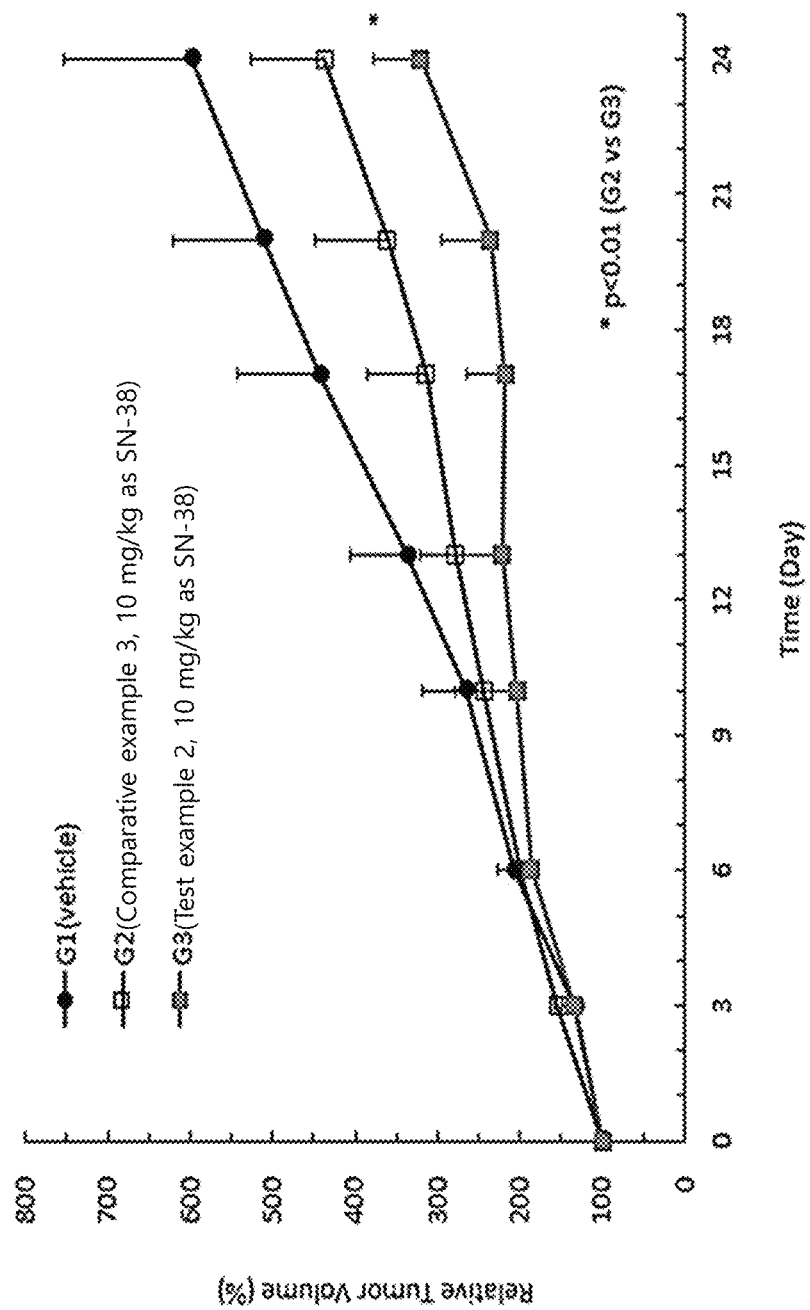

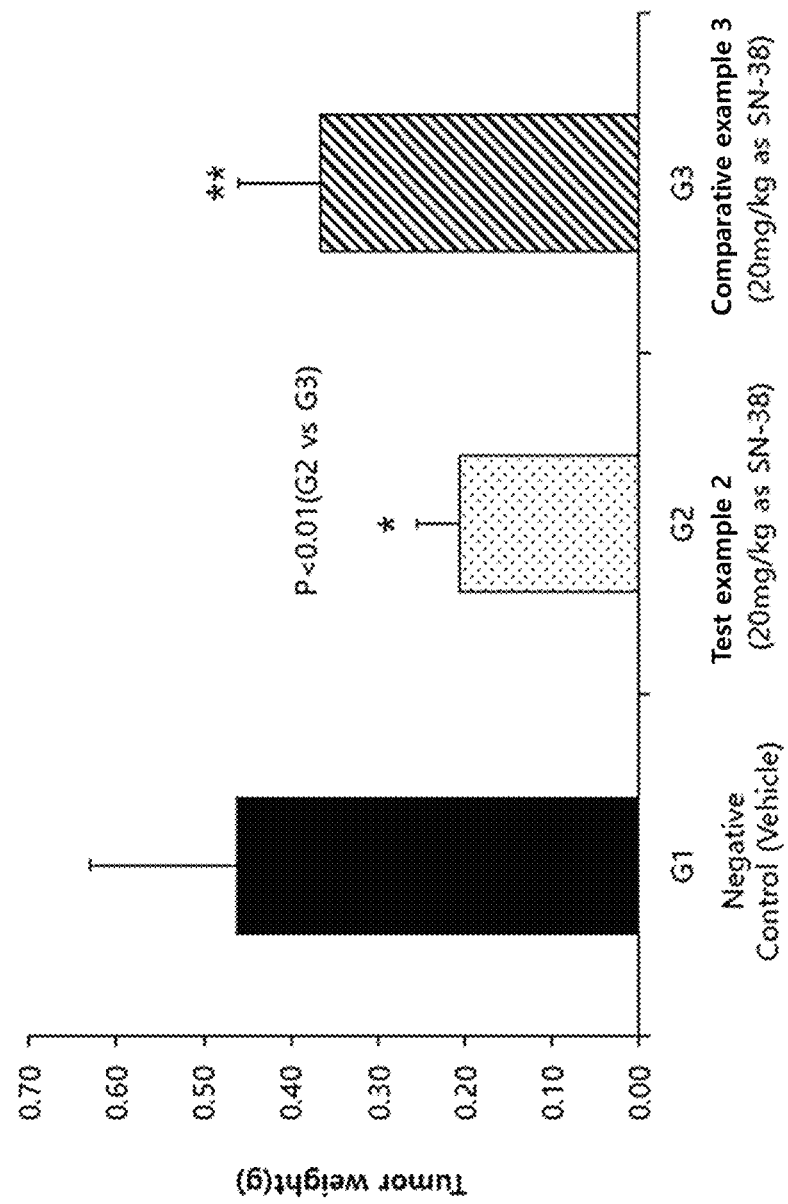

PARTICLE AND PHARMACEUTICAL COMPOSITION COMPRISING AN INSOLUBLE CAMPTOTHECIN COMPOUND WITH DOUBLE CORE-SHELL STRUCTURE AND METHOD FOR MANUFACTURING THE SAME

CROSS REFERENCE TO RELATED APPLICATIONS

This application is a divisional application of U.S. patent application Ser. No. 16/015,470 filed Jun. 22, 2018 (allowed), which claims priority to and the benefit of Korean Patent Application No. 10-2017-0079354 filed in the Korean Intellectual Property Office on 22 Jun. 2017, the disclosures of which are incorporated herein by reference.

TECHNICAL FIELD

The present disclosure relates to a drug delivery system having a double core-shell structure and, specifically, to a nano-drug delivery system having an inner core containing a poorly soluble camptothecin compound and a water-soluble camptothecin compound and an amphiphilic polymer shell, and to a manufacturing method therefor. Uses of the drug delivery system in treating cancer are disclosed.

BACKGROUND ART

A solubilizing step is essentially needed to develop a poorly soluble drug to be used for injection, and in order to overcome such a problem, emulsions containing surfactants, micro-emulsions, liposomes, micelles, pegylation, or making prodrugs, have been employed. 7-Ethyl 10-hydroxy camptothecin (SN-38), which is one of the drugs having strongest activity as camptothecin-based anticancer drugs, is supplied as irinotecan in a prodrug form (trade name: CAMTOSAR®, manufactured by Novartis), which is mainly hydrolyzed by carboxylesterase II (CESII) in vivo to be converted into SN-38 in an active form. However, the rate of conversion is as very low as 2-8% and the deviation thereof is also very large, and thus such a drug has difficulty in proper administration to cancer patients in need of precise dosage adjustment, with the result that the effects and side effects thereof are difficult to predict.

Another method for solubilization of a poorly soluble drug is to micellize a drug to have a nano-sized particle diameter. In order to allow a nanomicelle injection to secure sterility and stability, a nanomicelle aqueous solution is sterile-filtered through a 0.22-µm filter, and then powdered into solid through freeze-drying, during the manufacturing process. In this process, when a freeze-dried product is reconstituted for injection by dissolving the product in a solvent (saline or the like), a large amount of macroparticles (200 nm or more to several tens of µm) may be generated due to the agglomeration of micelles themselves. In particular, particles larger than 5 µm may cause severe side effects when injected into the human body, and thus are strictly managed through insoluble particulate matter tests in US Pharmacopoeia, European Pharmacopoeia, and Korean Pharmacopoeia. Therefore, a solubilizing method whereby the particle sizes are little changed before and after freeze-drying in spite of micellization, particles show a mono-distribution, and especially, there are no particles of several µm or more.

Meanwhile, it is essential to dissolve an active ingredient in an appropriate solvent for an injection, but camptothecin or SN-38, which is a hydrophobic camptothecin-based compound, is hardly dissolved in water or most volatile polar organic solvents (methanol, ethanol, acetonitrile, ethyl acetate, etc.) used in pharmaceutical formulation. Solvents capable of dissolving such the hydrophobic camptothecin-based compounds are limited to non-volatile solvents, such as dimethyl sulfoxide (DMSO), dimethyl formamide, toluene, and dioxane. However, these non-volatile solvents are toxic and, thus, required to be removed by complicate process such as a dialysis procedure. However, it is difficult to completely remove the non-volatile solvents, and residual solvents could cause side effects.

Therefore, the present inventors searched and endeavored to develop stable particle compositions of severely poorly soluble camptothecin compounds, which are free of the above problems and can be directly administered in an active form but not a prodrug form. Furthermore, there was a need for a severely poorly soluble camptothecin compounds nanoparticle formulation which does not undergo significant particle size changes before and after freeze-drying, and free of macro-agglomerated particles of several µm or more.

Throughout the entire specification, many patent documents are referenced and their citations are represented. The disclosures of cited papers and patent documents are entirely incorporated by reference into the present specification, and the level of the technical field within which the present invention falls and details of the embodiment are explained more clearly.

SUMMARY

An aspect of the present invention is to provide a particle including: i) a hydrophobic camptothecin-based compound; ii) a hydrophilic camptothecin-based compound; and iii) an amphiphilic block copolymer composed of a hydrophobic block and a hydrophilic block.

Another aspect of the present invention is to provide a pharmaceutical composition for treating cancer containing the particle and a pharmaceutically acceptable carrier.

Still another aspect of the present invention is to provide a method for manufacturing a particle, the method including:
(a) forming an inner core-shell containing a hydrophobic camptothecin-based compound and a hydrophilic camptothecin-based compound; and (b) forming an outer core-shell containing an amphiphilic copolymer.

According to another aspect, a method of treating cancer in a subject in need thereof which comprises administering an effective amount of the pharmaceutical composition to the subject.

Other purposes and advantages of the present disclosure will become more obvious with the following detailed description of the invention, claims, and drawings.

In accordance with an aspect of the present invention, there is provided Embodiments 1 to 35 below:
1. A particle comprising:
   i) a hydrophobic camptothecin-based compound;
   ii) a hydrophilic camptothecin-based compound; and
   iii) an amphiphilic block copolymer composed of a hydrophobic block and a hydrophilic block.
2. The particle of Embodiment 1, wherein the hydrophobic camptothecin-based compound is at least one selected from the group consisting of 7-ethyl-10-hydroxycamptothecin (SN-38), camptothecin, 10-hydroxycamptothecin, and a pharmaceutical acceptable salt thereof.

3. The particle of Embodiment 1, wherein the hydrophilic camptothecin-based compound is at least one selected from irinotecan, topotecan, belotecan, exatecan, lurtotecan, sinotecan, rubitecan, 9-nitrocamptothecin, 9-aminocamptothecin, gimatecan, BNP-1530, DB-67, BN-80915, BN-80927, a pharmaceutically acceptable salt thereof, a glucuronide metabolite thereof, and a glucuronide metabolite of the hydrophobic camptothecin-based compound.
4. The particle of Embodiment 1, wherein the amphiphilic block copolymer is composed of A-B or A-B-A blocks,
 (a) wherein A is a hydrophilic polymer, which is monomethoxy polyethylene glycol, dimethoxy polyethylene glycol, polyethylene glycol, polypropylene glycol, monomethoxy polypropylene glycol, polyethylene oxide, polyacrylic acid, or a polymer thereof; and
 (b) wherein B is a hydrophobic polymer, which is polylactic acid, polylactide, polyglycolic acid, polyglycolide, a polylactic acid-co-glycolic acid copolymer, polymandelic acid, polycaprolactone, polydioxan-2-one, polyglutamic acid, polyaspartic acid, polyornithine, polyorthoester, a derivative thereof, or a copolymer of two or more compounds selected therefrom.
5. The particle of Embodiment 4, wherein the number average molecular weight of the hydrophilic polymer A is 500-10,000 Da.
6. The particle of Embodiment 4, wherein the number average molecular weight of the hydrophobic polymer B is 500-10,000 Da.
7. The particle of Embodiment 1, wherein the weight ratio of the hydrophobic camptothecin-based compound and the hydrophilic camptothecin-based compound is 1:10 to 10:1.
8. The particle of Embodiment 1, wherein the weight ratio of the sum of the hydrophobic camptothecin-based compound and the hydrophilic camptothecin-based compound and the amphiphilic block copolymer is 1:200 to 10:1.
9. The particle of Embodiment 1, wherein the number average particle size of the particle is 10-500 nm.
10. The particle of Embodiment 1, wherein the particle has a double core-shell structure:
 (a) an inner core-shell containing the hydrophilic camptothecin-based compound and the hydrophobic camptothecin-based compound; and
 (b) an outer core-shell containing the amphiphilic block copolymer.
11. The particle of Embodiment 1, wherein the particle has a bilayer micelle structure.
12. A pharmaceutical composition for treating cancer, comprising the particle of any one of Embodiments 1 to 11 and a pharmaceutically acceptable carrier.
13. The composition of Embodiment 12, wherein the cancer is selected from the group consisting of gastric cancer, ovarian cancer, uterine cancer, small cell lung cancer, non-small cell lung cancer, pancreatic cancer, breast cancer, esophageal cancer, oral cancer, rectal cancer, colon cancer, large intestine cancer, kidney cancer, prostate cancer, melanoma, liver cancer, gall bladder and other biliary tract cancer, thyroid cancer, bladder cancer, brain and central nervous system cancer, bone cancer, skin cancer, non-Hodgkin's and Hodgkin's lymphoma, and blood cancer.
14. The composition of Embodiment 12, wherein the composition further comprises different types of anti-cancer drugs.
15. The composition of claim 12, further comprises sucrose, mannitol, sorbitol, glycerin, trehalose, and a polyethylene glycol excipient, and a cyclodextrin excipient.
16. A method for treating cancer in a subject, the method comprising administering an effective amount of the pharmaceutical composition of any one of Embodiments 1 to 15 to the subject.
17. The method of Embodiment 16, wherein the subject is human, mouse, rat, guinea pig, dog, cat, horse, cow, pig, monkey, chimpanzee, baboon, or rhesus monkey.
18. A method for manufacturing the particle of Embodiment 1, the method comprising:
 (a) forming an inner core-shell containing a hydrophobic camptothecin-based compound and a hydrophilic camptothecin-based compound; and
 (b) forming an outer core-shell containing an amphiphilic copolymer.
19. The method of Embodiment 18, wherein step (a) comprises mixing the hydrophobic camptothecin-based compound and a hydrophilic camptothecin-based compound in an organic solvent; and
 wherein step (b) comprises mixing the inner core-shell and the amphiphilic block copolymer in an aqueous solvent.
20. The method of Embodiment 18, wherein step (a) comprises mixing a basic aqueous solution, in which a hydrophobic camptothecin compound is dissolved, and an aqueous solution, in which a hydrophilic camptothecin compound is dissolved; and
 wherein step (b) comprises mixing the inner core-shell and the amphiphilic block copolymer in an aqueous solvent.
21. The method of Embodiment 20, wherein the aqueous solution in which the hydrophilic camptothecin compound is dissolved is a basic, neutral, or acidic aqueous solution.
22. The method of Embodiment 20, wherein step (a) comprises:
 (a1) mixing a basic aqeuous solution, in which a hydrophobic camptothecin-based compound is dissolved, and a basic, neutral, or acidic aqueous solution, in which a hydrophilic camptothecin-based compound is dissolved; and
 (a2) lowering the pH of the mixed aqueous solution to 7 or lower.
23. The method of Embodiment 18, wherein step (a) comprises mixing the hydrophobic camptothecin-based compound and the hydrophilic camptothecin-based compound in an organic solvent; and
 wherein step (b) comprises mixing a mixture of the hydrophobic camptothecin-based compound and the hydrophilic camptothecin-based compound with the amphiphilic block copolymer in an organic solvent.
24. The method of any one of Embodiments 18 to 23, wherein the hydrophobic camptothecin-based compound is at least one selected from the group consisting of 7-ethyl-10-hydroxycamptothecin (SN-38), camptothecin, 10-hydroxycamptothecin, and a pharmaceutical acceptable salt thereof.
25. The method of any one of Embodiments 18 to 24, wherein the hydrophilic camptothecin-based compound is at least one selected from irinotecan, topotecan, belotecan, exatecan, lurtotecan, sinotecan, rubitecan, 9-nitrocamptothecin, 9-aminocamptothecin, gimatecan, BNP-1530, DB-67, BN-80915, BN-80927, a pharmaceutically acceptable salt thereof, a glucuronide metabolite thereof, and a glucuronide metabolite of the hydrophobic camptothecin-based compound.
26. The method of any one of Embodiments 18 to 24, wherein the amphiphilic block copolymer is composed of A-B or A-B-A blocks,
   (a) wherein A is a hydrophilic polymer, which is monomethoxy polyethylene glycol, dimethoxy polyethylene glycol, polyethylene glycol, polypropylene glycol, monomethoxy polypropylene glycol, polyethylene oxide, polyacrylic acid, or a polymer thereof; and
   (b) wherein B is a hydrophobic polymer, which is polylactic acid, polylactide, polyglycolic acid, polyglycolide, a polylactic acid-co-glycolic acid copolymer, polymandelic acid, polycaprolactone, polydioxan-2-one, polyglutamic acid, polyaspartic acid, polyornithine, polyorthoester, a derivative thereof, or a copolymer of two or more compounds selected therefrom.
27. The method of Embodiment 26, wherein the molecular weight of the hydrophilic polymer A is 500-10,000 Da.
28. The method of Embodiment 26, wherein the molecular weight of the hydrophobic polymer B is 500-10,000 Da.
29. The method of any one of Embodiments 18 to 24, wherein the weight ratio of the hydrophobic camptothecin-based compound and the hydrophilic camptothecin-based compound is 1:10 to 10:1.
30. The method of any one of Embodiments 18 to 24, wherein the weight ratio of the sum of the hydrophobic camptothecin-based compound and the hydrophilic camptothecin-based compound and the amphiphilic block copolymer is 1:200 to 10:1.
31. The method of any one of Embodiments 18 to 24, wherein the organic solvent is a C1-C5 alcohol (methanol, ethanol, propanol, butanol, n-butanol, iso-propanol, 1-pentanol, 2-butoxyethanol, isobutyl alcohol, and etc), an alkyl acetate, acetone, acetonitrile, chloroform, benzene, toluene, xylene, acetone, fluoroalkane, pentane, hexane, 2,2,4-trimethylpentane, decane, cyclohexane, cyclopentane, diisobutylene, 1-pentene, 1-chlorobutane, 1-chloropentane, diisopropyl ether, 2-chloropropane, 1-chloropropane, chlorobenzene, benzene, diethyl ether, diethyl sulfide, dichloromethane, 1,2-dichloroethane, aniline, diethyl amine, an ether, carbon tetrachloride, tetrahydrofuran (THF), or a mixed solvent thereof.
32. The method of Embodiment 21 or 22, wherein the acidic aqueous solution includes at least one selected from pharmaceutically acceptable inorganic acids including hydrochloric acid, nitric acid, sulfuric acid, and phosphoric acid, or organic acids including citric acid, malic acid, lactic acid, acetic acid, and tartaric acid.
33. The method of Embodiment 21 or 22, wherein a pH of the acidic aqueous solution is 1.0 to 6.
34. The method of Embodiment 20, wherein the basic solution includes at least one selected from the group consisting of an inorganic alkali, an alkali salt of an organic acid, and an alkyl amine, the inorganic alkali including sodium hydroxide, potassium hydroxide, sodium dihydrogenphosphate, potassium dihydrogenphosphate, magnesium hydroxide, sodium carbonate, and sodium hydrogencarbonate.
35. The method of Embodiment 20, wherein a pH of the basic aqueous solution is 8 to 13.

BRIEF DESCRIPTION OF THE DRAWINGS

FIGS. 2 and 3 are a graph and images of extracted tumors, respectively, for comparing a tumor inhibitory effect of comparative core-shell particles (monolayer micelles) and inventive double core-shell particles (bilayer micelles) in colorectal cancer mouse models.
FIG. 4 is a graph for comparing a tumor inhibitory effect between comparative core-shell particles (monolayer micelles) and inventive double core-shell particles (bilayer micelles) in pancreatic cancer mouse models (AsPc-1, Xenograft).
FIGS. 5a and 5b are a graph and images of extracted tumors, respectively, for comparing a tumor inhibitory effect of comparative core-shell particles (monolayer micelles) and inventive double core-shell particles (bilayer micelles) in pancreatic cancer mouse models (MiaPaca-2, Orthotopic).

DESCRIPTION

Figure 1A:
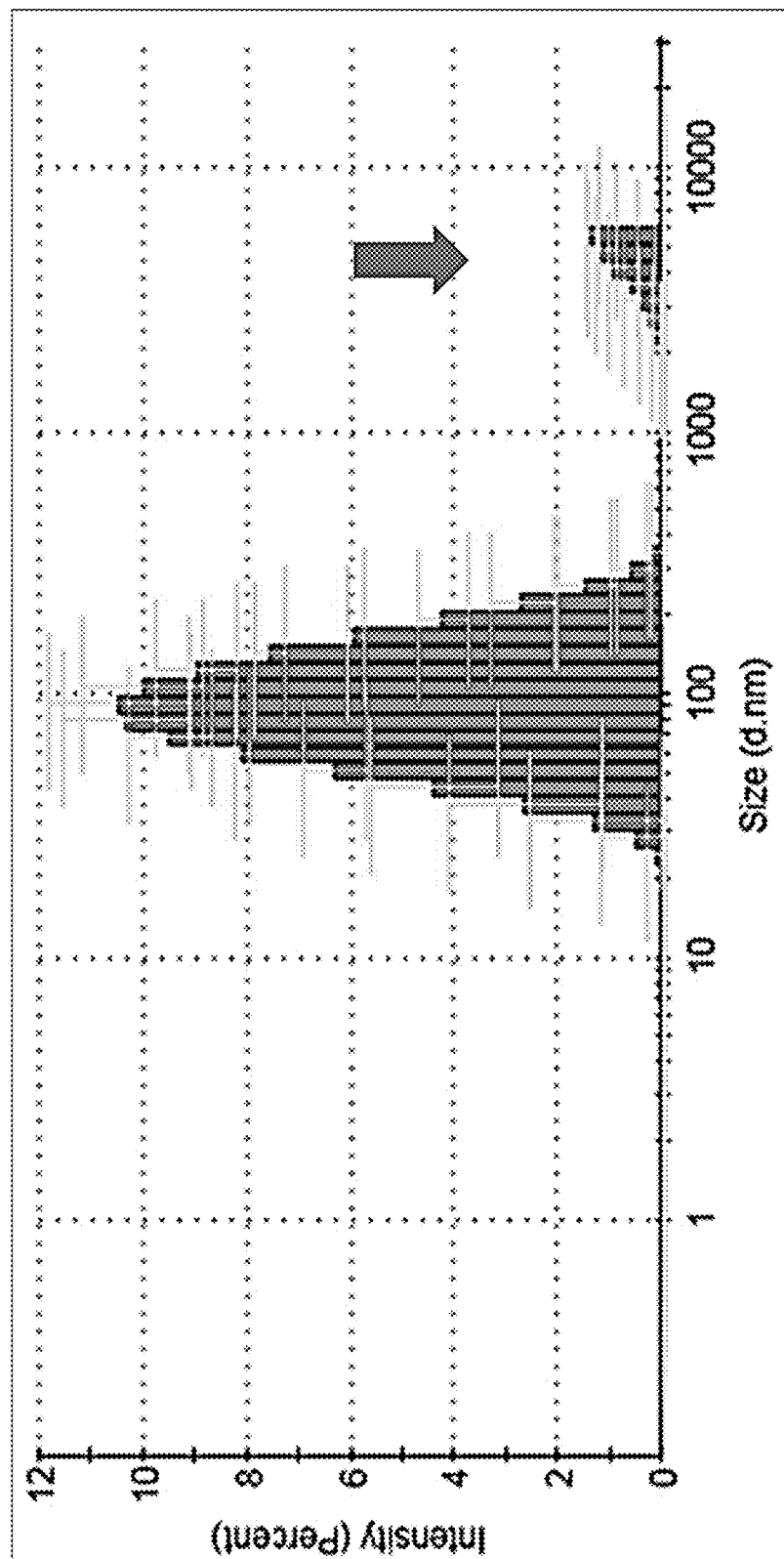
FIGS. 1a and 1b are graphs showing the dynamic light scattering (DLS) measurement results of the size distributions of particles in an aqueous solution after freeze-drying, with respect to comparative core-shell particles (monolayer micelles) composed of SN-38 and irinotecan.

The present inventors endeavored to improve the solubility and stability of a hydrophobic camptothecin-based compound, of which the application is restricted due to severe poor solubility thereof, in spite of strong anticancer activity thereof, and as a result, the present inventors confirmed that the mixing of a hydrophobic camptothecin-based compound and a hydrophilic camptothecin-based compound in an aqueous solvent or organic solvent leads to a core-shell like particle having core and shell structures formed of hydrophobic- and hydrophilic-based camptothecin compounds, respectively. Furthermore, it was confirmed that the addition of an amphiphilic block copolymer to the above core-shell particle forms a shell enclosing the particle. Throughout the disclosure, this structure that an inner particle formed from a combination of a hydrophobic camptothecin compound and a hydrophilic camptothecin compound is surrounded by a shell formed of an amphiphilic block copolymer is described as "double core-shell structure," "double core-shell particle," or "double micelle," or "bilayer micelle," which are interchangeably used herein.

According to an embodiment of the present invention, the double core-shell particle containing both of a hydrophobic camptothecin-based compound and a hydrophilic camptothecin-based compound has remarkably improved solubility compared with existing poorly soluble camptothecin even without administration in the form of a prodrug. Therefore, the drug efficacy of active camptothecin (SN-38) can be exerted regardless of the activity of carboxylesterase II (CESII) in vivo. In addition, it was confirmed that the particles caused no particle agglomeration or precipitation even though the particles are again dissolved in an aqueous solvent after freeze-drying, and thus the particles had a dosage form with very excellent stability. Therefore, an aspect of the present invention provides a particle composition with a stable double core-shell structure, which is advanced from an existing a monolayer nanomicelle to resolve a problem of low solubility of a poorly soluble drug.

In accordance with an aspect of the present invention, there is provided a particle comprising: i) a hydrophobic camptothecin-based compound; ii) a hydrophilic camptothecin-based compound; and iii) an amphiphilic block copolymer composed of a hydrophobic block and a hydrophilic block.

Herein, camptothecin is a topoisomerase inhibitor found in bark and stalk of the Camptotheca tree (Happy tree) and exhibits a very excellent anticancer effect in the preclinical stage, but cannot be used due to low solubility thereof. Therefore, many researchers have developed camptothecin analogues to improve the solubility of camptothecin. Currently, three types of camptothecin derivatives, irinotecan, topotecan, and belotecan, have been approved for cancer chemotherapy.

As used herein, the term "hydrophobicity" refers to the exclusion from water molecules and agglomeration, as a tendency shown in non-polar materials. When a hydrophobic material is present in a hydrophilic liquid, the hydrophobic material agglomerates while increasing hydrophobic bonds as if the hydrophobic material is afraid of water.

As used herein, the term "hydrophilicity" refers to the property of being dissolved in water with strong affinity with water, as a tendency shown in polar materials. For example, a hydrophilic polymer compound, or a micelle colloid surface of a surfactant has strong hydrophilicity.

According to an embodiment, the hydrophobic camptothecin-based compound is selected from the group consisting of 7-ethyl-10-hydroxycamptothecin (SN-38), camptothecin, 10-hydroxycamptothecin, and a pharmaceutical acceptable salt thereof, but is not limited thereto.

According to another embodiment of the present invention, the hydrophilic camptothecin-based compound is selected from irinotecan, topotecan, belotecan, exatecan, lurtotecan, sinotecan, rubitecan, 9-nitrocamptothecin, 9-aminocamptothecin, gimatecan, BNP-1530, DB-67, BN-80915, BN-80927, a pharmaceutically acceptable salt thereof, a glucuronide metabolite thereof, and a glucuronide metabolite of the hydrophobic camptothecin-based compound, but is not limited thereto.

According to a specific embodiment of the present invention, the hydrophobic camptothecin-based compound, which constitutes the inner particle, may be camptothecin, SN-38, or a mixture thereof, and the hydrophilic camptothecin-based compound, which also constitutes the inner particle together with the hydrophobic camptothecin-based compound, may be irinotecan hydrochloride, topotecan hydrochloride, and a glucuronide analog of SN-38.

As used herein, the term "copolymer" refers to a polymer prepared from two or more different types of monomers. For example, the reaction of styrene acrylonitrile in a reaction container results in a copolymer having both of the two monomers. The term "block copolymer" refers to a copolymer having a form in which a block of one type of monomers is linked to a block of another type of monomers. A case in which a block of material A is followed by a block of material B is expressed by -[-AB-]-. A chain is called AB type if the chain is composed of only one strand of each monomer, ABA type if A blocks are present at both ends of B block in the center, and ABC type if three different types of blocks are present in a main chain. A block copolymer is mainly formed by ionic polymerization. Unlike other copolymers, this block copolymer has many physical properties of a homopolymer formed from two types of monomers.

According to an embodiment of the present invent, the amphiphilic block copolymer constituting the particle of the present invention is composed of block A-B or block A-B-A. Here, A is a hydrophilic polymer, which is monomethoxy polyethylene glycol, dimethoxy polyethylene glycol, polyethylene glycol, polypropylene glycol, monomethoxy polypropylene glycol, polyethylene oxide, polyacrylic acid, or a polymer thereof, but is not limited thereto. In addition, B is a hydrophobic polymer, which is polylactic acid, polylactide, polyglycolic acid, polyglycolide, a polylactic acid-co-glycolic acid copolymer, polymandelic acid, polycaprolactone, polydioxan-2-one, polyglutamic acid, polyaspartic acid, polyornithine, polyorthoester, a derivative thereof, or a copolymer of two or more compounds selected therefrom, but is not limited thereto. It would be obvious to a person skilled in the art that any compound that can constitute an amphiphilic block copolymer usable in the art can be used without limitation.

In a specific embodiment of the present invention, the amphiphilic block copolymer is PEG-PCL [poly(ethylene glycol)-b-poly(carprolactone)]; PEG-PLA [poly(ethylene glycol)-b-poly(lactic acid)]; mPEG-PGA [monomethoxy poly(ethylene glycol)-b-poly(glycolic acid)]; mPEG-PLGA [monomethoxy poly(ethylene glycol)-b-poly(lactide-co-glycolide)]; PEG-PBLA [poly(ethylene glycol)-b-poly(β-benzyl-L-aspartic acid)]; PEG-p(Glu) [poly(ethylene glycol)-b-poly(glutamic acid)]; PEG-p(Asp) [poly(ethylene glycol)-b-poly(aspartic acid)]; and/or PEG-PLA-PEG [poly(ethylene glycol)-b-poly(lactic acid)-b-poly(ethylene glycol).

According to an embodiment of the present invention, the hydrophilic polymer A and the hydrophobic polymer B each has a number average molecular weight of 500-10,000 Da, and more specifically 1,000-7,000 Da. When the number average molecular weights of the hydrophilic polymer A and the hydrophobic polymer B are less than 500 Da or more than 10,000 Da, the produced particles have an average size of 200 nm or more and exhibit a multimodal distribution, and thus are difficult to be a nanoparticle drug prescribed by the US FDA.

According to another embodiment of the present invention, the weight ratio of the hydrophobic camptothecin-based compound and the hydrophilic camptotechin-based compound, which constitute the particle of the present invention, is 1-10:1-10, 1-10:1-5, 1-10:1-3, 1-10:1, 1-5:1-10, 1-3:1-10, or 1:1-10, specifically 1-5:1-5, 1-5:1-3, 1-5:1, 1-3:1-5, or 1:1-5, and more specifically 1-3:1-3, 1-3:1, or 1:1-3, but is not limited thereto.

According to an embodiment of the present invention the weight ratio of (a) the sum of the hydrophobic camptothecin-based compound and the hydrophilic camptotechin-based compound and (b) the amphiphilic block copolymer is 1:0.1-200, 1:0.5-200 1:1-200, 1:2-200, 1:5-200, 1:10-200, 1:50-200, 1:100-200, 1:150-200, 1:0.1-100, 1:0.5-100, 1:1-100, 1:2-100, 1:5-100, 1:10-100, 1:20-100, 1:50-100, 1:0.1-50, 1:0.5-50, 1:1-50, 1:5-50, 1:10-50, 1:20-50, 1:0.1-20, 1:0.5-20, 1:1-20, 1:5-20, 1:10-20, 1:0.1-10, 1:0.5-10, or 1:1-10.

As used herein, the term "to" or "-" between two numerical values means a section between the numerical values including numerical values described before and after the term.

Meanwhile, the particle of the embodiments has a double core-shell structure comprising the following:
  (a) an inner core-shell containing the hydrophilic camptothecin-based compound and the hydrophobic camptothecin-based compound; and (b) an outer core-shell containing the amphiphilic block copolymer.

In addition, the particle of an embodiment of the present invention has a bilayer micelle structure.

The amphiphilic block copolymer in which a hydrophilic block and a hydrophobic block are combined at a particular ratio is known to form a micelle through self-assembly in an aqueous solution. The inside of the micelle is hydrophobic, and thus the amphiphilic block copolymer is applied as a drug delivery system for a poorly soluble preparation. A polystyrene-polyethylene oxide double block copolymer (PS-b-PEO) is well known to form a spherical micelle having an insoluble core (PS) and a soluble shell (PEO) in water.

As described above, the particle of the present invention includes (a) a hydrophilic camptothecin-based compound and a hydrophobic camptothecin-based compound; and (b) an amphiphilic block copolymer.

As proved in an example of the present invention, the mixing of the hydrophilic camptothecin-based compound and the hydrophobic camptothecin-based compound significantly increases solubility in aqueous solvents and forms particles. Here, it is likely that the hydrophilic camptothecin-based compound serves as a hydrophilic block of the amphiphilic copolymer, and the hydrophobic camptothecin-based compound serves as a hydrophobic block of the amphiphilic copolymer, constituting a core-shell structure (micelle).

Therefore, the particle of the present invention forms a double micelle (double core-shell) containing: a monolayer micelle inside; and an amphiphilic block copolymer containing the monolayer micelle inside, wherein in the monolayer micelle, a hydrophilic camptothecin-based compound and a hydrophobic camptothecin-based compound constitute a core-shell structure. More specifically, the hydrophobic block of the amphiphilic block copolymer constitutes an insoluble core toward the monolayer micelle, which is relatively hydrophobic and composed of camptothecin-based compounds, and the hydrophilic block constitutes a soluble shell toward an external aqueous solvent, and as a result, a double core-shell structured double micelle is formed.

According to an embodiment of the present invention, the double core-shell structured particles spontaneously form particles when dispersed in an aqueous solution.

According to an embodiment of the present invention, the number average particle size of the particles is 10-500 nm, 10-400 nm, 10-300 nm, or 10-200 nm, and more specifically 20-500 nm, 20-400 nm, 20-300 nm, or 20-200 nm. The number average particle size of the particles of the present invention shows limited change even before or after the particles are freeze-dried. The reason seems that the hydrophobic and hydrophilic camptothecin-based compounds primarily constitute an inner core-shell structured micelle and the amphiphilic block copolymer secondarily constitutes an outer shell surrounding the micelle, so that during the freeze-drying, the secondary outer shell serves as a cryoprotectant that prevents rapid crystallization, agglomeration, particle collapse of the primary inner core-shell. As a result, the particles of the present invention cause no agglomeration or precipitation even when the particles are again dissolved in the aqueous solvent after freeze-drying. Therefore, the present invention provides a stable double core-shell structured particle composition, which is advanced from an existing a monolayer nanomicelle to resolve a problem of solubility of a severely poorly soluble drug.

According to another aspect of the present invention, the present invention provides a pharmaceutical composition for treating cancer, the pharmaceutical composition comprising the foregoing particles and a pharmaceutically acceptable carrier.

In an embodiment of the present invention, the cancer is selected from the group consisting of gastric cancer, ovarian cancer, uterine cancer, small cell lung cancer, non-small cell lung cancer, pancreatic cancer, breast cancer, esophageal cancer, oral cancer, rectal cancer, colon cancer, large intestine cancer, kidney cancer, prostate cancer, melanoma, liver cancer, gall bladder, and other biliary tract cancer, thyroid cancer, bladder cancer, brain and central nervous system cancer, bone cancer, skin cancer, non-Hodgkin's and Hodgkin's lymphoma.

When the particles of embodiments of the present invention or the composition containing the same is prepared into a pharmaceutical composition, the pharmaceutical composition of the present invention may contain a pharmaceutically acceptable carrier. The pharmaceutically acceptable carrier is normally used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil. The pharmaceutical composition of the present invention may further contain a lubricant, a wetting agent, a sweetening agent, a flavoring agent, an emulsifier, a suspending agent, a preservative, and the like, in addition to the above ingredients. Suitable pharmaceutically acceptable carriers and agents are described in detail in *Remington's Pharmaceutical Sciences* (19th ed., 1995).

In a specific embodiment of the present invention, the pharmaceutical composition of the present invention may further contain sucrose, mannitol, sorbitol, glycerin, trehalose, a polyethylene glycol-based excipient, and a cyclodextrin-based excipient (alpha-, beta-, and gamma-cyclodextrin, hydroxy cyclodextrin, or a cyclodextrin derivative). The excipient is added to the particles, which correspond to an active ingredient of the present pharmaceutical composition, serves as a cryoprotectant or an osmoregulator, and is formulated by freeze-drying, solvent evaporation, or the like.

The pharmaceutical composition of an embodiment of the present invention may be administered orally or parenterally, and examples of parenteral administration may include intravenous administration, subcutaneous administration, intradermal administration, intramuscular administration, intranasal administration, mucosal administration, intradural administration, intraperitoneal administration, intraocular administration, and the like, and specifically, the pharmaceutical composition of the present invention may be administered intravenously.

The suitable dose of the pharmaceutical composition of an embodiment of the present invention varies depending on factors, such as a formulating method, a manner of administration, patient's age, body weight, gender, morbidity, and food, a time of administration, a route of administration, an excretion rate, and response sensitivity. The ordinarily skilled practitioners can easily determine and prescribe the dose that is effective for the desired treatment or prevention. According to an embodiment of the present invention, the daily dose of the pharmaceutical composition of the present invention is 0.001-100 mg/kg.

The pharmaceutical composition of an embodiment of the present invention may be formulated into a unit dosage form or may be prepared in a multi-dose container by using a pharmaceutically acceptable carrier and/or excipient according to a method that is easily conducted by a person having an ordinary skill in the art to which the present invention pertains. Here, the dosage form may be a solution in an oily or aqueous medium, a suspension, an emulsion, an extract, a powder, granules, a tablet, or a capsule, and may further contain a dispersant or a stabilizer.

The pharmaceutical composition of an embodiment of the present invention may be administered in parallel with a known compound or pharmaceutical composition having a cancer treatment effect.

In an embodiment of the present invention, the composition further contains another type of anticancer drug. Specifically, the composition of the present invention further contains a poorly soluble anticancer drug, such as paclitaxel or docetaxel.

The poorly soluble anticancer drugs represented by paclitaxel and docetaxel have low utilization due to poor solubility, like the above-mentioned camptothecin, but the poorly soluble anticancer drugs have remarkably improved solubility when contained in the double micelle particles of an embodiment of the present invention. Therefore, the particle of an embodiment of the present invention per se is a camptothecin-based anticancer drug, and can be favorably used as a drug delivery system platform, which can load poorly soluble anticancer drugs or novel candidate drugs with low solubility problems to improve solubility thereof.

According to still another aspect of the present invention, the present invention provides a method for cancer treatment, the method comprising administering the foregoing pharmaceutical composition of the present invention to a subject in need thereof.

As used herein, the term "administration" or "administer" refers to the direct application of a therapeutically effective amount of the composition to a subject (i.e., an object) with cancer, thereby forming the same amount thereof in the body of the subject.

The term "therapeutically effective amount" of the composition refers to the content of the composition, which is sufficient to provide a therapeutic or preventive effect to a subject to be administered, and thus the term has a meaning including "prophylactically effective amount." As used herein, the term "subject" includes, but is not limited to, human, mouse, rat, guinea pig, dog, cat, horse, cow, pig, monkey, chimpanzee, baboon, or rhesus monkey. Specifically, the subject of the present invention is human.

Since the method for cancer treatment of an embodiment the present invention includes a step of administering the pharmaceutical composition for cancer treatment according to an aspect of the present invention, the overlapping descriptions therebetween are omitted to avoid excessive complication of the specification.

According to another aspect of the present invention, there is provided a method for manufacturing a particle, the method comprising:
(a) forming an inner core-shell containing a hydrophobic camptothecin-based compound and a hydrophilic camptothecin-based compound; and
(b) forming an outer core-shell containing an amphiphilic copolymer.

In an embodiment of the present invention, step (a) comprises mixing the hydrophobic camptothecin-based compound and a hydrophilic camptothecin-based compound in an organic solvent; and step (b) comprises mixing the inner core-shell and the amphiphilic block copolymer in an aqueous solvent.

Since the hydrophobic camptothecin-based compound is severely hydrophobic, a particular solubilizing technique or preparation method is needed. In an example of the present invention, in order to overcome such poor solubility, a hydrophobic camptothecin-based compound and a hydrophilic camptothecin-based compound were, primarily, simultaneously dissolved in an organic solvent, and then an organic solvent was completely removed by utilizing a rotary vacuum evaporator, thereby obtaining a film form mixture of camptothecin-based compounds. Here, a small amount of aqueous solvent (e.g., distilled water) was added thereto with intensive mixing using a vortex-mixer or with ultrasonication, thereby obtaining a nano-sized inner core-shell particle.

Then, an amphiphilic polymer previously dissolved in an aqueous solvent (e.g., distilled water) was added to the inner core-shell particle, followed by homogeneous and vigorous mixing using a vortex-mixer or ultrasonication, thereby obtaining nano-sized double core-shell particles. Finally, a cryoprotectant and an isotonizing agent was added thereto to be completely dissolved therein, and then the resultant solution was filtered through a 0.22-μm sterile filter, followed by freeze-drying. When added to a 0.9% sodium chloride injection, a 5% glucose injection, or injection water, the final freeze-dried material is self-assembled to form double core-shell particles with a number average particle size of 20-200 nm.

In the case where the particles manufactured according to the present invention have a particle size of 200 nm or less, the non-selective removal of a reticuloendothelial (RES) system in the body can be avoid, and thus it is preferable to manufacture particles having a uniform particle size of 200 nm or less.

In another embodiment of the present invention, step (a) comprises mixing a basic aqueous solution, in which a hydrophobic camptothecin compound is dissolved, and an aqueous solution, in which a hydrophilic camptothecin compound is dissolved; and step (b) comprises mixing the inner core-shell and the amphiphilic block copolymer in an aqueous solvent to form an amphiphilic block copolymer shell surrounding the inner core-shell.

Here, the aqueous solution in which the hydrophilic camptothecin compound is dissolved may be a basic, neutral, or acidic aqueous solution.

The inner core-shell can be manufactured by the following method besides the manufacturing method in an organic solvent. The hydrophobic camptothecin-based compound (e.g., camptothecin, SN-38) has very low solubility in an acidic or neutral aqueous solution of pH 7 or less, but the solubility of the hydrophobic camptothecin-based compound is rapidly increased in a basic aqueous solution since a lactone ring is opened to have a form of carboxylic acid. Therefore, the hydrophobic camptothecin-based compound is dissolved in the basic aqueous solution, and then an aqueous solution in which a hydrophilic camptothecin-based compound is dissolved is added thereto to lower the pH to 7 or less, so that the hydrophobic camptothecin-based compound and the hydrophilic camptothecin-based compound form a micelle, and the acidity is neutralized and the lactone ring is closed, thereby restoring to the original chemical structure thereof.

In a specific embodiment of the present invention, step (a) comprises: (a1) mixing a basic aqueous solution, in which a hydrophobic camptothecin-based compound is dissolved, and a basic, neutral, or acidic aqueous solution, in which a hydrophilic camptothecin-based compound is dissolved; and (a2) lowering the pH of the mixed aqueous solution to 7 or lower.

In an example of the present invention, camptothecin or SN-38 is dissolved in a basic aqueous solution, and a hydrophilic camptothecin-based compound previously dissolved in an aqueous solution is added to the basic aqueous solution with vigorous mixing using ultrasonication or a vortex-mixer, and an acidic aqueous solution is further added thereto to adjust the pH to 7 or less, thereby obtaining core-shell particles formed from the hydrophoic and the hydrophilic camptothecin compounds. An amphiphilic polymer previously dissolved in an aqueous solvent (e.g., distilled water) is added to the produced core-shell particles through vortex-mixing or ultrasonication, thereby manufacturing a double core-shell particle. A cryoprotectant and an isotonizing agent is further added thereto to be dissolved therein, followed by sterile filtration using a 0.22-μm filter, and followed by freeze-drying.

In the manufacturing method of an embodiment of the present invention, the acidic aqueous solution contains a pharmaceutically acceptable inorganic acid, such as hydrochloric acid, nitric acid, sulfuric acid, or phosphoric acid, and at least one organic acid selected from the group consisting of citric acid, malic acid, lactic acid, acetic acid, and tartaric acid. The pH of the acidic aqueous solution is 1-6. In addition, the manufacturing method of an embodiment of the present invention, the basic aqueous solution contains: an inorganic alkali, including sodium hydroxide, potassium hydroxide, sodium dihydrogenphosphate, potassium dihydrogenphosphate, magnesium hydroxide, sodium carbonate, and sodium hydrogencarbonate; an alkali salt of an organic acid; an alkyl amine; or a mixture thereof. The pH of the basic aqueous solution is 8-13.

In still another embodiment of the present invention, step (a) includes mixing the hydrophobic camptothecin-based compound and the hydrophilic camptothecin-based compound in an organic solvent; and step (b) includes mixing a mixture of the hydrophobic camptothecin-based compound and the hydrophilic camptothecin-based compound with an amphiphilic block copolymer in an organic solvent.

In the embodiments, step (a) (manufacturing of inner core-shell) and step (b) (manufacturing of external amphiphilic copolymer shell) can be performed in one step.

An example of the present invention shows a method for simultaneously manufacturing the inner core-shell and the outer amphiphilic copolymer shell. A hydrophobic camptothecin (e.g., 10-hydroxycamptothecin or SN-38), together with a hydrophilic camptothecin (e.g., irinotecan hydrochloride), is added into an organic solvent, and completely dissolved with stirring, and an amphiphilic block copolymer (e.g., mPEG-PLA) previously dissolved in an organic solvent is added thereto with stirring. The mixture solution was dried by a rotary vacuum evaporator, and an aqueous solvent (e.g., distilled water) is added to residues, followed by ultrasonication in an ultrasonic cleaner for 10 minutes, thereby manufacturing particles in which the hydrophilic camptothecin and the hydrophobic camptothecin together form the inner core-shell and the amphiphilic block copolymer forms a surrounding shell.

In the manufacturing method of particles, the definitions of a hydrophobic camptothecin-based compound, a hydrophilic camptothecin-based compound, and an amphiphilic block copolymer, which constitute the particles, are as described above with respect to the particles of embodiments of the present invention.

In the manufacturing method of the present invention, the organic solvent is a C1-C5 alcohol (methanol, ethanol, propanol, butanol, n-butanol, iso-propanol, 1-pentanol, 2-butoxyethanol, isobutyl alcohol, etc.), an alkyl acetate, acetone, an acetonitrile, chloroform, benzene, toluene, xylene, acetone, a fluoroalkane, pentane, hexane, 2,2,4-trimethyl pentane, a decane, a cyclohexane, diisobutylene, 1-pentene, 1-chlorobutane, 1-chloropentane, diisopropyl ether, 2-chloropropane, 1-chloropropane, chlorobenzene, benzene, diethyl ether, diethyl sulfide, dichloromethane, 1,2-dichloroethane, an aniline, a diethyl amine, an ether, carbon tetrachloride, tetrahydrofuran (THF), or a mixed solvent thereof, but is not limited thereto.

The double core-shell structured particles manufactured by the present invention do not precipitate into crystals even when diluted to a sufficiently low concentration in an aqueous solution, leading to very stable particles. The particles of embodiments of the present invention show a mono-distribution of particles in an injection solvent before and after freeze-drying. The proportion of particles of 200 nm or more is 10% or less, and particles of 500 nm or more are not present. Furthermore, the particles according to embodiments of the present invention show excellent results, compared with existing monolayer micelles in animal efficacy tests and pharmacokinetic tests, and does not use a surfactant (Cremophore EL, Pluronic, etc.) causing hypersensitivity, and thus the use of the particles of the embodiments can provide a pharmaceutical composition or a drug delivery system platform, which are safe for the human body.

MODE FOR CARRYING OUT THE INVENTION

Hereinafter, various embodiments of the present invention will be described in detail with reference to examples. These examples are only for illustrating the present invention more specifically, and it will be apparent to those skilled in the art that the scope of the present invention is not limited by these examples.

EXAMPLES

Throughout the present specification, the term "%" used to express the concentration of a specific material, unless otherwise particularly stated, refers to (wt/wt) % for solid/solid, (wt/vol) % for solid/liquid, and (vol/vol) % for liquid/liquid.

Materials

Among the compounds used in the present invention, hydrophobic and hydrophilic camptothecin-based compounds, polysaccharides such as trehalose, cyclodextrin, polyethylene glycol, and the like were used from Sigma-Aldrich, AbCem, Toronto Research Chemical (Canada) or Tocris (USA), and polymers were used from Akina Inc (USA), Advanced Polymer Materials (Canada), Shanghai Liang Chemical Co., LTD (China), NanoSoft Polymer (USA), and Samyang BioPharm (Korea).

Example 1: Solubility in Different Solvents, when Hydrophobic Camptothecin Compound was Dissolved Alone or Hydrophobic Camptothecin Compound and Hydrophilic Camptothecin Compound were Dissolved in Mixture The solubility change according to solvent was measured when the hydrophobic camptothecin compound, camptothecin or 7-ethyl-10-hydroxy-camptothecin (SN-38) was dissolved alone or together with the hydrophilic camptothecin-based compound, irinotecan (CPT-11), topotecan, or belotecan (CKD-602).

1) Solubility in Different Solvents when Hydrophobic Camptothecin Compound was Dissolved Alone A supersaturated solution was prepared by adding 20 mg of the hydrophobic camptothecin compound (camptothecin or SN-38) to 5 ml of ethanol, acetonitrile, acetone, ethyl acetate, chloroform dimethyl sulfoxide, or distilled water, followed by ultrasonic treatment for 30 minutes. The prepared supersaturated solution was filtered through a 0.45-μm filter, and a filtrate was properly diluted, followed by HPLC analysis.

2) Solubility in Different Solvents when Hydrophobic Camptothecin Compound and Hydrophilic Camptothecin Compound were Dissolved in Mixture The present inventors prepared a supersaturated solution by adding 20 mg of the hydrophilic camptothecin compound (irinotecan hydrochloride, topotecan hydrochloride, or belotecan) to 5 ml of ethanol, acetonitrile, chloroform, ethyl acetate, dimethyl sulfoxide, or distilled water, and then adding 20 mg of the hydrophobic camptothecin compound (SN-38 or camptothecin), followed by ultrasonication for 30 minutes. The prepared supersaturated solution was filtered through a 0.45-μm filter, and a filtrate was properly diluted, followed by HPLC analysis.

HPLC (Agilent 1200 Series, USA) conditions were as follows. The column was CapcellPak C8 (5 m, 4.6 mm×25 cm, Shiseido); the mobile phase was a mixed solvent of methanol:acetonitrile:buffer (2.8 g/L sodium dihydrogenphosphate, 1.8 g/L 1-octanesulfonate aqueous solution)=17:24:59 (v/v); the flow rate was 1.5 mL/min; the measurement wavelength was UV 255 nm; and the sample injection amount was 15 μL. The solubility test results are shown in table 1 below.

hydrochloride, topotecan hydrochloride, or belotecan, had solubility increased up to 15-fold, which corresponds to an appropriate level of solubility required for the manufacture of drugs. It was therefore confirmed from the above results that the solubility of the hydrophobic camptothecin compounds was remarkably increased when dissolved in mixing with a hydrophilic camptothecin compound.

Example 2: Manufacturing of Core-Shell from Hydrophobic Camptothecin-Based Compound and Hydrophilic Camptothecin-Based Compound in Organic Solvent and Evaluation of Particle Size In the present example, the hydrophobic camptothecin-based compound camptothecin or SN-38, and the hydrophilic camptothecin-based compound irinotecan hydrochloride, topotecan hydrochloride, belotecan, or SN-38-glucuronide, or an amphiphilic polymer (PEG-PBLA) were dissolved in an organic solvent to manufacture core-shell particles, and an amphiphilic polymer was added thereto to form a shell surrounding the core-shell particles.

1) Manufacturing of Core-Shell Particles (Comparative Examples 1 to 6)

The core-shell particles were manufactured by using, as a main ingredient, a hydrophobic camptothecin (camptothecin or SN-38), and water-soluble camptothecin (irinotecan hydrochloride, topotecan hydrochloride, or SN-38-glucuronide) as an active ingredient or an amphiphilic polymer (poly(ethyleneglycol)-poly (β-butyrolactone-co-lactic acid); PEG-PBLA), as shown in table 2 below.

Specifically, 20 mg of water-soluble camptothecin (irinotecan hydrochloride, topotecan hydrochloride, or SN-38 glucuronide) or PEG-PBLA was added to 20 mg of hydrophobic camptothecin, and 100 ml of an organic solvent (a 50:50 mixture solution of ethanol and acetonitrile) was added thereto to attain complete dissolution, followed by drying in a rotary vacuum evaporator. 20 ml of distilled water was added to the dried product, followed by ultrasonication at 20-30° C. for 20 minutes in an ultrasonic cleaner (UC-20, 20 Hz, 400 W, Jeio Tech, Korea), thereby

TABLE 1

Solubility changes of hydrophobic camptothecin-based compounds in polar organic solvents (unit: mg/ml)

| Solvent type | Comparative example Camptothecin 20 mg — | Inventive example Camptothecin 20 mg Irinotecan 20 mg | Comparative example SN-38 20 mg — | Inventive example SN-38 20 mg Irinotecan 20 mg | Inventive example SN-38 20 mg Topotecan 20 mg | Inventive example SN-38 20 mg Belotecan 20 mg |
|---|---|---|---|---|---|---|
| Ethanol | 0.149 | 1.414 | 0.779 | 2.885 | 2.205 | 2.047 |
| Acetonitrile | 0.101 | 1.090 | 0.402 | 1.972 | 1.694 | 1.338 |
| Chloroform | 0.002 | 0.051 | 0.009 | 0.025 | 0.088 | 0.104 |
| Ethyl acetate | 0.134 | 0.295 | 0.078 | 0.425 | 0.239 | 0.221 |
| Dimethyl sulfoxide | 3.291 | >4 | 2.263 | 3.816 | 2.949 | 2.685 |
| Distilled water | 0.009 | 0.011 | <0.001 | <0.001 | <0.001 | <0.001 |

As shown in Table 1 above, the poorly soluble compound camptothecin or SN-38 alone was hardly dissolved in most solvents including water, and were dissolved at 2.26-3.29 mg/mL in only dimethyl sulfoxide (DMSO) as a non-volatile solvent. However, camptothecin or SN-38, when dissolved together with the relatively hydrophilic drug, irinotecan obtaining nano-sized particles containing the camptothecin compound and the PEG-PBLA shell enclosing the camptothecin compound (also referred to as "monolayer micelles" or "comparative core-shell" herein) in a dispersed state in an aqueous solution. 600 mg of D-trehalose was added to the aqueous solution containing the nano-sized particles, thereby attaining complete dissolution, and then the solution was filtered through a 0.22 μm sterile filter, and the filtrate was freeze-dried. The freeze-drying was conducted for a total of 62 hours under a temperature cycle of −45° C.→−20° C.→0° C.→20° C. at a vacuum pressure of 100 mTorr or lower, and a freeze-drier from Operon (Korea) was used. An aliquot of the prepared freeze-dried product was taken, and again dissolved in distilled water for injection, and the size of particles was measured by the dynamic light scattering (DLS) (Zetasizer™, Malvern, UK).

2) Manufacturing of Inventive Core-Shell Particles (Inventive Examples 1 to 4)

In order to prepare a bilayer particle composition having a double core-shell structure, the present inventors added 20 mg of each of hydrophobic camptothecin and hydrophilic camptothecin into 100 ml of an organic solvent (a 50:50 mixture solution of ethanol and acetonitrile) to be dissolved therein, followed by drying using a rotary vacuum evaporator (Buchi). 200 ml of distilled water was added to the dried product, followed by ultrasonication at 20-30° C. for 20 minutes in an ultrasonic cleaner, thereby obtaining nano-sized core-shell particles formed form the mixture of hydrophobic camptothecin and hydrophilic camptothecin (also referred to as "inner particle" or "inner core-shell" or "inner core" herein) in a dispersed state in an aqueous solution. While the aqueous solution mixed with the inner core-shell particles was stirred, 90 mg of the amphiphilic block copolymer methoxy poly(ethylene glycol)-poly(lactide) (mPEG-PLA) (mPEG molecular weight:PLA molecular weight=2,000:1,500) previously dissolved in 10 ml of distilled water was slowly added, followed by stirring at 20-30° C. for 6 hours, thereby preparing double core-shell particles having a structure that an amphiphilic block copolymer shell surrounds the inner core-shell (also referred to as "double core-shell," "double core-shell particle," or "bilayer micelle" herein), in a dispersed state in an aqueous solution. 600 mg of D-trehalose as a cryoprotectant was added to the aqueous solution containing double core-shell particles to be dissolved therein, and then the mixture was filtered through a 0.22-μm sterile filter, and then freeze-drying was conducted by the same method as in the manufacturing of primary core-shell particles, thereby obtaining a freeze-dried product as a white powder. A predetermined amount of the freeze-dried product was again dissolved in injection water to measure the size of the particles. In addition, the average particle sizes after/before freeze-drying were measured, and the proportion of particle with 200 nm or more and the distribution pattern (mono- or multi-modal distribution) were compared.

TABLE 2

Proportions in manufacturing of particles (unit: mg)

| | Micelle type | Poorly soluble camptothecin Camptothecin | SN-38 | Water-soluble camptothecin Irinotecan hydrochloride | Topotecan hydrochloride | SN-38 glucuronide | PEG-PBLA (5k: 6.5k) | mPEG-PLA (2k:1.5k) |
|---|---|---|---|---|---|---|---|---|
| Comparative example 1 | Mono- | 20 | — | 20 | — | — | — | — |
| Comparative example 2 | Mono- | 20 | — | — | — | 20 | — | — |
| Inventive example 1 | Bi- | 20 | — | 20 | — | — | — | 90 |
| Comparative example 3 | Mono- | — | 20 | 20 | — | — | — | — |
| Comparative example 4 | Mono- | — | 20 | — | 20 | — | — | — |
| Comparative example 5 | Mono- | — | 20 | — | — | 20 | — | — |
| Comparative example 6 | Mono- | — | 20 | — | — | — | 20 | — |
| Inventive example 2 | Bi- | — | 20 | 20 | — | — | — | 90 |
| Inventive example 3 | Bi- | — | 20 | — | 20 | — | — | 90 |
| Inventive example 4 | Bi- | — | 20 | — | — | 20 | — | 90 |

*PEG-PBLA: poly (ethylene glycol) -b-poly (ß-benzyl-L-aspartic acid)
*mPEG-PLA: methoxypoly (ethylene glycol) -b-poly (lactic acid)

TABLE 3

Comparision results of particle size and distribution before/after freeze-drying in particles

| | Micelle type | Particle size before freeze-drying (n = 3) Average particle size (nm) | >200 nm Propotion (%) | Particle size after freeze-drying (n = 3) Average particle size (nm) | >200 nm proportion (%) | >1 μm | Pariticle distribution |
|---|---|---|---|---|---|---|---|
| Comparative | Mono- | 123.9 | 5.9 | 156.1 | 40.1 | ◯ | Multi- |

TABLE 3-continued

Comparision results of particle size and distribution before/after freeze-drying in particles

| | Micelle type | Particle size before freeze-drying (n = 3) | | Particle size after freeze-drying (n = 3) | | | |
|---|---|---|---|---|---|---|---|
| | | Average particle size (nm) | >200 nm Propotion (%) | Average particle size (nm) | >200 nm proportion (%) | >1 μm | Pariticle distribution |
| example 1 | | | | | | | |
| Comparative example 2 | Mono- | 133.6 | 7.1 | 152.8 | 38.6 | ○ | Multi- |
| Inventive example 1 | Bi- | 135.8 | 3.6 | 148.9 | 4.8 | ND | Mono- |
| Comparative example 3 | Mono- | 76.2 | 0.0 | 108.4 | 16.4 | ○ | Multi- |
| Comparative example 4 | Mono- | 78.5 | 0.1 | 115.4 | 28.5 | ○ | Multi- |
| Comparative example 5 | Mono- | 92.1 | 2.7 | 131.2 | 30.4 | ○ | Multi- |
| Comparative example 6 | Mono- | 102.8 | 5.9 | 138.4 | 34.2 | ○ | Multi- |
| Inventive example 2 | Bi- | 83.3 | 0.0 | 93.8 | 2.4 | ND | Mono- |
| Inventive example 3 | Bi- | 88.2 | 0.1 | 99.8 | 2.8 | ND | Mono- |
| Inventive example 4 | Bi- | 93.3 | 0.2 | 105.4 | 3.1 | ND | Mono- |

*ND: Not detected

As shown in Table 3 above, as for the average particle size after freeze-drying, the comparative core-shell particles (monolayer micelles) composed of poorly soluble camptothecin and water-soluble camptothecin or the primary core-shell particles composed of poorly soluble camptothecin and an amphiphilic polymer were increased to about 1.2- to 1.5-fold, but the inventive double-core-shell particles (bilayer micelles) only increased about 1.1-fold.

Figure 1B:
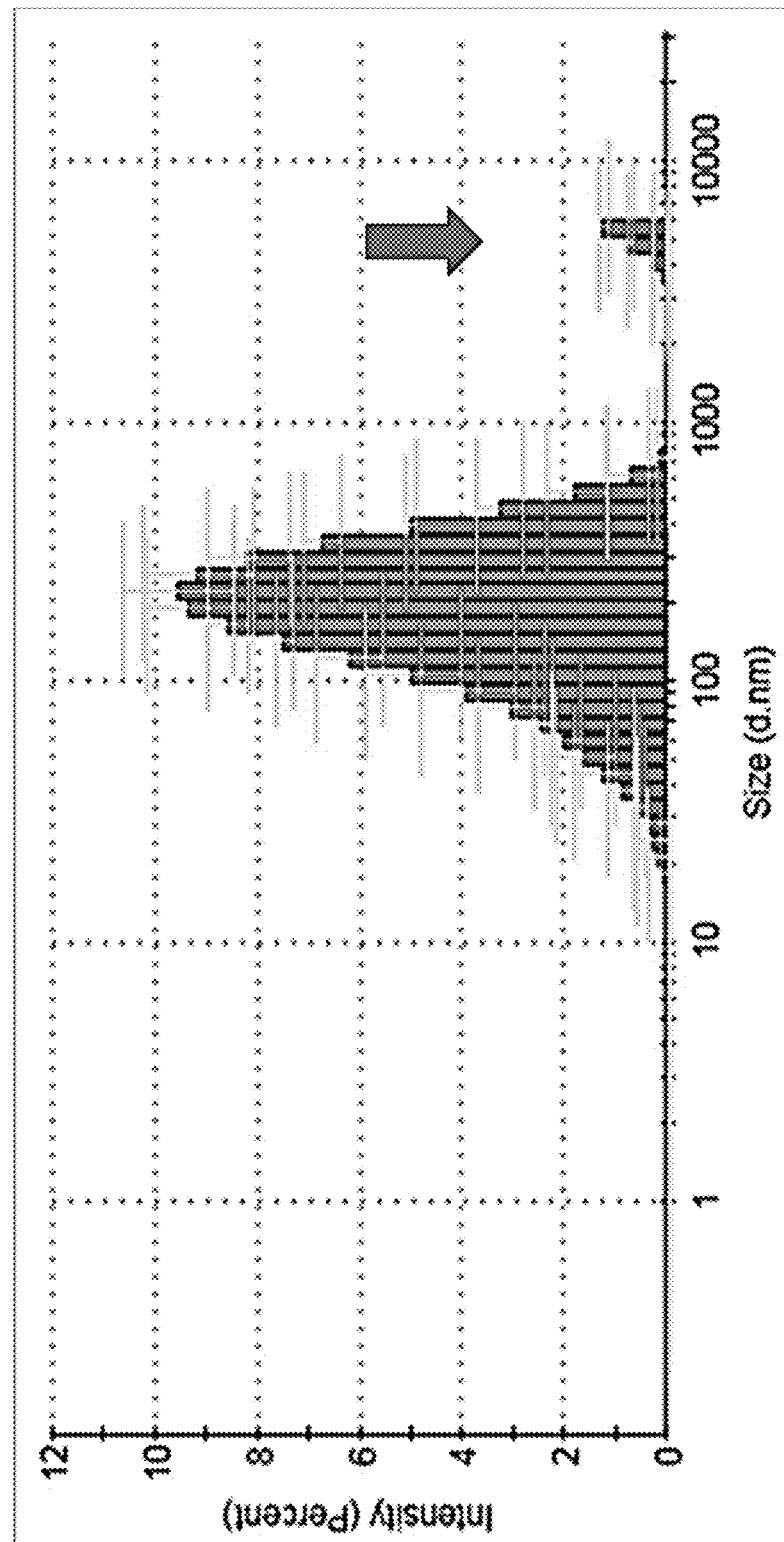

With respect to the comparative core-shell particles (monolayer micelles), after the freeze-drying, the particles of 200 nm or more were produced in large amounts, about 16-40%, and especially, the particles of several micrometers (μm) or more, capable of influencing safety when administered to the human body, were produced (comparative examples 1 to 6 on table 3 and FIGS. 1a and 1b). Whereas, with respect to inventive double core-shell particles, the particles of 200 nm or more were detected in about 2.4-3.1% for SN-38 and about 4.8% for camptothecin, both being less than 5%, showing very favorable results, and the particles of 500 nm or more were not observed (Inventive examples 1 to 4 in table 3, and FIG. 1c).

Figure 1C:
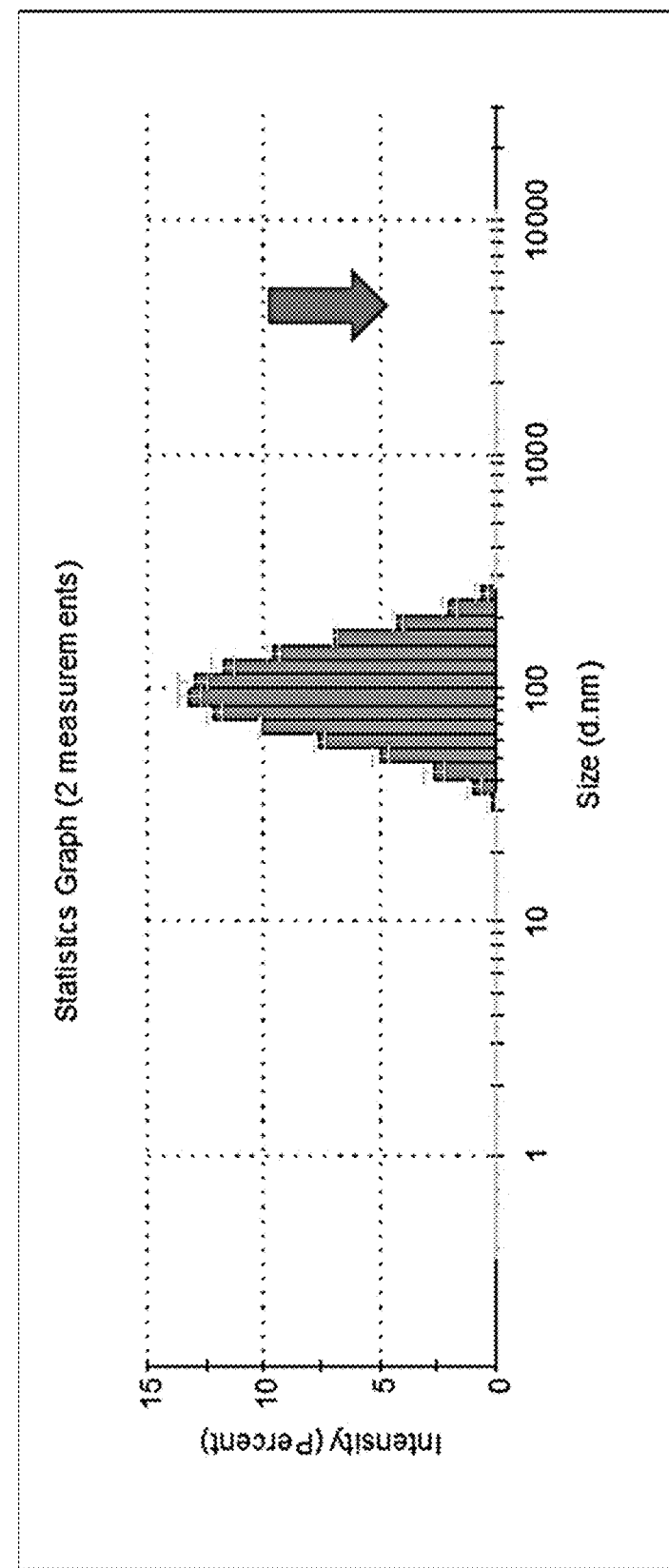
FIG. 1c is a graph showing the dynamic light scattering (DLS) measurement results of the size distributions of particles in an aqueous solution after freeze-drying, with respect to inventive double core-shell particles (bilayer micelle) prepared according to an exemplary embodiment.

In the particular distribution, the comparative core-shell particles (monolayer micelles) showed a distribution with multiple peaks (FIGS. 1a and 1b), but the inventive core-shell particles showed a mono-distribution, confirming a very stable structure (FIG. 1c). In addition, the average particle size of the comparative core-shell particles (monolayer micelles) was smaller than that of the inventive double core-shell particles (bilayer micelles) by about 10 nm before freeze-drying, but the change of the particle size before and after freeze-drying was very great, whereas the inventive double core-shell particles (bilayer micelles) were very physically stable.

Example 3: Evaluation of Stability of Comparative Core-Shell Particles and Inventive Double Core-Shell Particles In the present example, monolayer micelles (comparative examples 1, 3, and 6) and double core-shell particles (inventive examples 1 and 2) were compared for the change in particle size over the time. Sample products manufactured according to the drug stability test standards were stored for six months in accelerated test conditions (40° C., 75% relative humidity). The results are shown in Table 4.

TABLE 4

Test results of stability of Comparative core-shell particles (monolayer micelles) and Inventive double core-shell particles (bilayer micelles)

| | Micelle type | 0 month | | 3 months | | 6 months | |
|---|---|---|---|---|---|---|---|
| | | Average particle size (nm) | >200 nm Propotion (%) | Average particle size (nm) | >200 nm Propotion (%) | Average particle size (nm) | >200 nm Propotion (%) |
| Comparative example 1 | Mono- | 156.1 | 40.1 | 172.1 | 47.6 | 196.6 | 58.1 |
| Inventive example 1 | Bi- | 148.9 | 4.8 | 155.0 | 5.6 | 168.3 | 7.4 |

TABLE 4-continued

Test results of stability of Comparative core-shell particles
(monolayer micelles) and Inventive double core-shell particles
(bilayer micelles)

| | Micelle type | 0 month | | 3 months | | 6 months | |
|---|---|---|---|---|---|---|---|
| | | Average particle size (nm) | >200 nm Propotion (%) | Average particle size (nm) | >200 nm Propotion (%) | Average particle size (nm) | >200 nm Propotion (%) |
| Comparative example 3 | Mono- | 108.4 | 16.4 | 126.7 | 28.1 | 151.9 | 31.6 |
| Comparative example 6 | Mono- | 138.4 | 34.2 | 149.9 | 44.6 | 174.2 | 48.4 |
| Inventive example 2 | Bi- | 93.8 | 2.4 | 99.5 | 3.5 | 112.9 | 3.8 |

The comparative core-shell particles (monolayer micelles), containing camptothecin or SN-38 as a main ingredient, and inventive double core-shell particles (bilayer micelles) were subjected to stability tests. As a result, in the case of the monolayer micelles, the average particle size was increased by about 50% or more and the proportion of the particles of 200 nm or more was rapidly increased to 58% in accelerated test conditions. In the case of the bilayer particles, the average particle size was increased by about 20%, and the proportion of the particles of 200 nm or more was restricted within 3.8% for SN-38 and 7.4% for camptothecin. Therefore, it can be seen that the structure of the inventive particles according to embodiments of the present invention was significantly improved in view of stability, compared with the comparative particles.

Example 5: Manufacturing of Double Core-Shell Particles According to Type of Amphiphilic Polymer and Molecular Weight of Amphiphilic Polymer In the present example, inventive double core-shell particles were manufactured using various amphiphilic polymers (block copolymers). As shown in Table 5, 20 mg of each of SN-38 and irinotecan hydrochloride as hydrophobic and hydrophilic camptothecin compounds, 500 mg of trehalose as a cryoprotectant, and 90 mg of each of amphiphilic polymers were used. The manufacturing method was carried out in the same manner as in the core-shell particle manufacturing method in example 2 above, and the materials were again dissolved in injection water after freeze-drying to compare particular sizes.

TABLE 5

Particle size comparision of bilayer particles after freeze-drying
according to amphiphilic polymer type and average molecular weight thereof

| No | Polymer type (Average molecular weight) | Particle size (nm) | >200 nm Proportion (%) | >1 μm presence or absence | Particle distribution (Mono-/Multi-) | PDI |
|---|---|---|---|---|---|---|
| Inventive example 5 | PEG-PCL (5k:2.5k) | 133.8 | 5.0 | ND | Mono- | 0.271 |
| Inventive example 6 | PEG-PCL(2k:1.5k) | 102.0 | 3.1 | ND | Mono- | 0.209 |
| Inventive example 7 | PEG-PLA(2.5k:1k) | 99.2 | 2.9 | ND | Mono- | 0.225 |
| Inventive example 8 | mPEG-PGA (2k: 1.5k) | 99.7 | 2.6 | ND | Mono- | 0.213 |
| Inventive example 9 | mPEG-PLGA (1k: 1k) | 101.5 | 3.4 | ND | Mono- | 0.247 |
| Inventive example 10 | PEG-PBLA (5k: 6.5k) | 137.9 | 9.8 | ND | Mono- | 0.287 |
| Inventive example 11 | PEG-p (Glu) (5k:2.5k) | 122.1 | 6.5 | ND | Mono- | 0.245 |
| Inventive example | mPEG-p (Asp) (5k:2.5k) | 128.2 | 7.6 | ND | Mono- | 0.231 |

TABLE 5-continued

Particle size comparision of bilayer particles after freeze-drying according to amphiphilic polymer type and average molecular weight thereof

| No | Polymer type (Average molecular weight) | Particle size (nm) | >200 nm Proportion (%) | >1 μm presence or absence | Particle distribution (Mono-/Multi-) | PDI |
|---|---|---|---|---|---|---|
| 12 Inventive example 13 | PEG-PLA-PEG (2.5k-1k-2.5k) | 156.4 | 11.8 | ND | Mono- | 0.298 |

*PEG-PCL: poly(ethylene glycol)-b-poly(caprolactone)
*PEG-PLA: poly(ethylene glycol)-b-poly(lactic acid)
*mPEG-PGA: monomethoxy poly(ethylene glycol)-b-poly(glycolic acid)
*mPEG-PLGA: monomethoxy poly(ethylene glycol)-b-poly(lactide-co-glycolide)
*PEG-PBLA: poly(ethylene glycol)-b-poly(ß-benzyl-L-aspartic acid)
*PEG-p (Glu): poly(ethylene glycol)-b-poly(glutamic acid)
*PEG-p (Asp): poly(ethylene glycol)-b-poly(aspartic acid)
*PEG-PLA-PEG: poly(ethylene glycol)-b-poly(lactic acid)-b-poly(ethylene glycol)
*PDI: Polydiversity index As shown in Table 5 above, it can be seen that the inventive particles of embodiments of the present invention can be manufactured by using various amphiphilic polymers (block copolymers) and amphiphilic polymers having various average molecular weights, and the stability of the particles was excellent.

Example 6: Evaluation of Particle Size According to Type of Cryoprotectant

In the present example, the effects of a cryoprotectant in the manufacturing of freeze-dried double core-shell particles were observed. Here, 10-hydroxycamptothecin and SN-48 were selected as hydrophobic camptothecin compounds; irinotecan hydrochloride was selected as a hydrophilic camptothecin; and mPEG-PLA (2 k:1.5 k) was used as an amphiphilic polymer. As a cryoprotectant, 500 mg of each of D-trehalose, D-mannitol, PEG2000, and hydroxypropyl-β-cyclodextrin (HP-b-CD) was used. The double core-shell particles were manufactured using the compositions shown in Table 6, and the manufacturing method was carried out in the same manner as in example 2.

TABLE 6

Size of double core-shell particles according to cryoprotectant type

| | 10-OH Camptothecin (mg) | SN-38 (mg) | Irinotecan (mg) | mPEG-PLA | Cryoprotectant (500 mg) | Particle size (nm) | >200 nm Proporiton (%) | >1 μm presence or absence |
|---|---|---|---|---|---|---|---|---|
| Inventive example 13 | 20 | — | 20 | 90 | Mannitol | 121.8 | 4.4 | ND |
| Inventive example 14 | — | 20 | 20 | 90 | Mannitol | 101.1 | 2.9 | ND |
| Inventive example 15 | 20 | — | 20 | 90 | Trehalose | 118.6 | 5.8 | ND |
| Inventive example 16 | — | 20 | 20 | 90 | Trehalose | 99.6 | 3.1 | ND |
| Inventive example 17 | — | 20 | 20 | 90 | PEG2000 | 133.2 | 19.6 | ○ |
| Inventive example 18 | — | 20 | 20 | — | PEG2000 | 164.9 | 32.8 | ○ |
| Inventive example 19 | — | 20 | 20 | 90 | HP-b-CD | 126.8 | 9.3 | ○ |
| Inventive example 20 | — | 20 | 20 | — | HP-b-CD | 151.7 | 26.2 | ○ |

*PEG2000: Polyethyleneglycol 2000
*HP-b-CD: hydroxypropyl-ß-cyclodextrin
*ND: Not detected As shown in Table 6, favorable results were observed in view of the particle size when the polysaccharides mannitol and trehalose were used as cryoprotectants. Whereas, the particle sizes were somewhat large, for example, particles with a size of 1 μm or more were detected, in PEG2000 and HP-b-CD. In inventive examples 18 and 20 for monolayer micelles, relatively large particle of 200 nm or more and macroparticles of 1 μm or more were observed when polyethylene glycol and cyclodextrin were used as cryoprotectants.

Example 7: Manufacturing of Inner Core-Shell Particles and Double Core-Shell Particles in Water-Soluble Solvent Conditions The inner core-shell particles can be manufactured in an aqueous solution as well as an organic solvent as in example 2. As shown in Table 7 below, 10 mg of SN-38 was completely dissolved in 0.1 ml of a 0.5 M sodium hydroxide aqueous solution, and the resultant solution was dropped and neutralized in an aqueous solution of irinotecan hydrochloride (1 mg/ml) previously dissolved in 15 ml of a 0.5 mM hydrochloride aqueous solution, and a hydrochloride aqueous solution was further added to control the pH to about 5, followed by ultrasonication, thereby obtaining inner core-shell particles. 40 mg of the amphiphilic polymer mPEG-PLA was added thereto, followed by stirring at room temperature for 6 hours, and 300 mg of D-trehalose was further added to be dissolved. The mixture solution was filtered through a 0.22-μm sterile filter, freeze-dried, and again dissolved in injection water, and then the particle size was measured (inventive example 21). SN-38 and irinotecan were dissolved using the organic alkali ethanol amine as a basic aqueous solution or the organic acid citric acid as an acidic aqueous solution, and bilayer particles were manufactured by the same method, thereby measuring the particle sizes, respectively (inventive examples 22 and 23).

placed together with 20 mg of irinotecan hydrochloride in 100 ml of an organic solvent (50:50 mixture solution of ethanol:acetonitrile), and completely dissolved with stirring, and 90 mg of mPEG-PLA (2 k:1.5 k) dissolved in 10 ml of an organic solvent (50:50 mixture solution of ethanol: acetonitrile) was added thereto with stirring. The mixture solution was dried by a rotary vacuum evaporator, and 200 ml of distilled water was added to residues, followed by ultrasonication for 10 minutes in an a ultrasonic cleaner, thereby obtaining double core-shell particles of the embodiment. 400 mg of D-mannitol as a cryoprotectant was added to be dissolved, and this solution was filtered through a 0.22-μm sterile filter, freeze-dried. A proper amount of the freeze-dried product was again dissolved in injection water to measure the particle size. The results are shown in Table 8.

TABLE 7

Manufacturing of bilayer particles under basic and acidic aqueous solutions

| | SN-38 (mg) | Irinotecan (mg) | Trehalose | mPEG-PLA (2k:1.5k) | Type of acid and basic solvents and particle size (nm) | | |
|---|---|---|---|---|---|---|---|
| | | | | | NaOH/ HCl | Ethanolamine/ HCl | NaOH/ Citric acid |
| Inventive example 21 | 10 | 10 | 300 | 40 | 120.1 | — | — |
| Inventive example 22 | 10 | 10 | 300 | 40 | — | 122.3 | — |
| Inventive example 23 | 10 | 10 | 300 | 40 | — | — | 119.5 |

As shown in Table 7, the double core-shell particles manufactured by dissolving hydrophobic camptothecin and hydrophilic camptothecin in basic and acidic aqueous solutions showed a particle size of about 120 nm, and thus the double core-shell particles were successfully manufactured.

Example 8: Mixing Manufacturing of Double Core-Shell Particles

The present example showed a method for manufacturing double core-shell particles by mixing all the hydrophobic camptothecin, hydrophilic camptothecin, and amphiphilic block copolymer in one step. Hydrophobic camptothecin compounds (10-hydroxycamptothecin and SN-38) were

TABLE 8

Particle size of double core-shell particles (bilayer micelles) produced by mixing manufacturing

| | SN-38 (mg) | 10-OH Camptothecin (mg) | Irinotecan (mg) | mPEG-PLA (mg) | D-mannitol (mg) | Particle size (nm) | >200 nm Proportion (%) | >1 μm Presence or absence |
|---|---|---|---|---|---|---|---|---|
| Inventive example 24 | 20 | — | 20 | 90 | 400 | 125.4 | 4.2 | ND |
| Inventive example 25 | — | 20 | 20 | 90 | 400 | 129.3 | 4.8 | ND |

*ND: Not detected

As shown in Table 8, the double core-shell particles manufactured by simultaneously mixing and dissolving hydrophobic camptothecin, hydrophilic camptothecin, and amphiphilic polymer in an organic solvent showed a monodistribution of particle sizes of about 120-130 nm, wherein particles of 200 nm or more were detected in small amounts, 5% or less, but particles of 1 μm or more were not detected, and thus the particles were confirmed to have overall favorable stability.

Example 9: Tumor Inhibitory Effect Comparison Test of Comparative Core-Shell Particles and Inventive Double Core-Shell Particles in Tumor Mouse Models (Colorectal Cancer)

In colorectal mouse models, compositions comprising the monolayer micelle of comparative examples 3 and 6 and compositions comprising bilayer particles of inventive example 2 were measured for anticancer effect by the following method.

Figure 2:
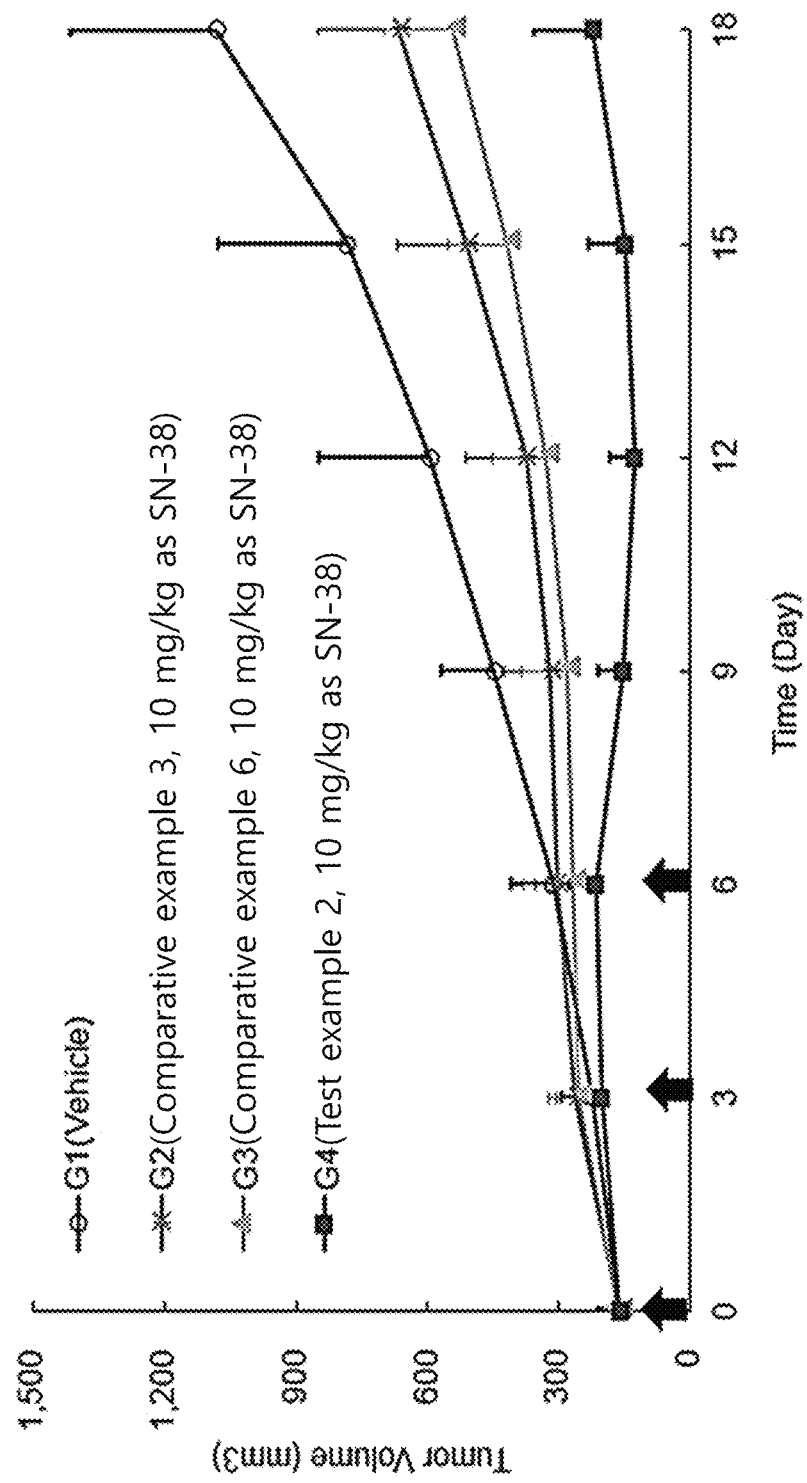

The previously cultured colorectal cancer cell line (HT-29) was injected at $5 \times 10^6$ cells/0.2 mL into the right flank of Balb/c nude mice, and after about 7 days, only tumors with a size of 150-200 mm$^3$ were selected. Nine animals were assigned to each group, and were intravenously administered with a sham drug (non-treatment group), comparative example 3 (monolayer micelles), comparative example 6 (monolayer micelles), and inventive example 2 (bilayer particles), once every three days, three times in total. The dose was 10 mg/kg on the basis of SN-38. The volume of tumor measured every three days after the administration of the test composition was used as a measurement index of the anticancer effect, and was observed for a total of 18 days. The results are shown in FIGS. 2 and 3.

As a result of measurement of tumor inhibitory effect, the monolayer micelle compositions (comparative examples 3 and 6) showed a tumor inhibitory effect of about 50-60% compared with a negative control group, and the bilayer particle composition (inventive example 2) showed a tumor inhibitory effect of about 80% or more compared with a negative control group, indicating very excellent effects. These results were due to the fact that the stabilized micelle structure and the micelle structure having a size as small as 200 nm or less of the embodiment were efficiently transferred to cancer tissues while stably staying in the body.

Example 10: Tumor Inhibitory Effect Comparison Test of Comparative Core-Shell Particle and Inventive Bilayer Particles in Pancreatic Cancer Mouse Models (AsPc-1)

The tumor inhibitory effect of a composition comprising the monolayer micelle (comparative core-shell particle) of comparative example 3 was compared with that of a composition comprising the bilayer particles of inventive example 2) in pancreatic cancer mouse models. The previously cultured pancreatic cancer cell line (AsPc-1) was injected at $5 \times 10^6$ cells/0.2 mL into the right flank of male BALB/c-nu/nu mice, and after about 10 days, only tumors with a size of 100-150 mm$^3$ were selected. Ten animals were assigned to each group, and were administered with a sham drug (non-treatment group), comparative example 3, and inventive example 2, once every seven days, three times in total. The dose was 10 mg/kg on the basis of SN-38. The volume of tumor measured every three days after the administration of the test composition was used as a measurement index of the anticancer effect, and was observed for a total of 24 days. The results are shown FIG. 4.

As a result of measurement of tumor inhibitory effect, the monolayer micelle composition (comparative example 3) showed a tumor inhibitory effect of about 27% compared with a negative control group, and the bilayer particle composition (inventive example 2) showed a tumor inhibitory effect of about 47% or more compared with a negative control group, indicating very excellent effects. The results were overall similar to those in the colorectal cancer models (Example 9), and it was confirmed that the bilayer particle composition of the embodiment were very excellent in tumor inhibitory effects compared with monolayer micelles.

Example 11: Tumor Inhibitory Effect Comparison Test of Comparative Core-Shell Particle Composition and Inventive Bilayer Particle Composition in Pancreatic Cancer Mouse Models (MiaPaca-2)

Figure 5B:
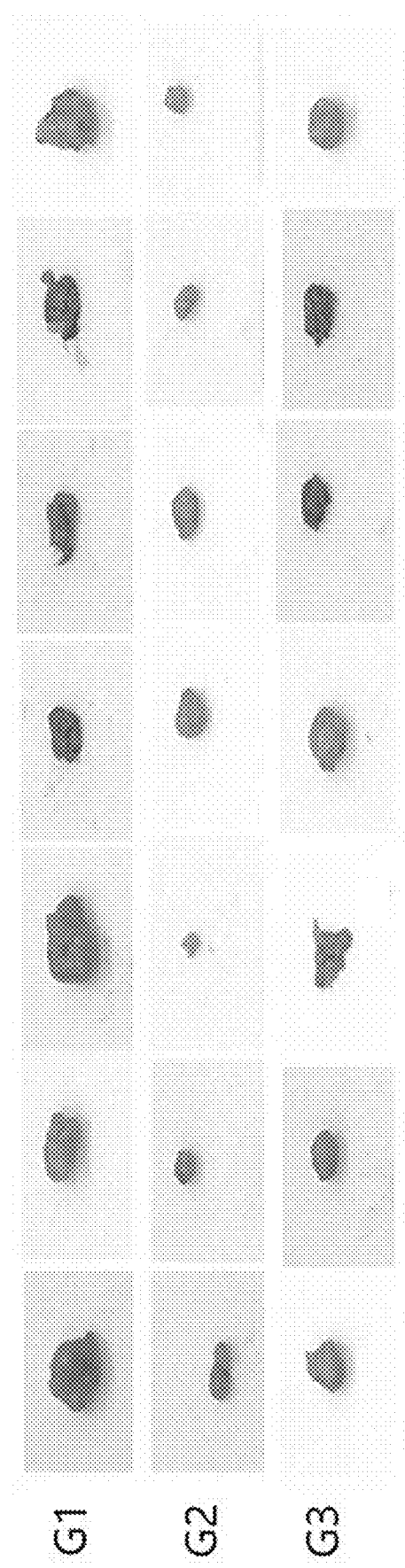

The tumor inhibitory effect of a composition comprising the monolayer micelle (comparative core-shell particle) of comparative example 3 was compared with that of the bilayer particle composition (inventive example 2) in pancreatic cancer mouse models (Orthotopic) on the basis of SN-38. After the left flank side of male BALB/c-nu/nu mice was incised at 0.7-1 cm, the entire pancreas and spleen were exposed to the outside, and then the pancreatic cancer cell line (MiaPaca-2 cell line) previously cultured using a syringe was injected at $1 \times 10^7$ cells/0.1 mL. It was confirmed that the tumor cell suspension did not leak, and the organs exposed to the outside were relocated again, and the incision site was sutured by suture thread. About 10 days after the inoculation of the pancreatic cancer cell line, grouping was carried out by the body weight. Ten animals were assigned to each group, and were administered with a sham drug (non-treatment group), comparative example 3, and test example 2, once every seven days, three times in total. The dose was 20 mg/kg on the basis of SN-38. The animals were observed for a total of 28 days, and the tumor size and weight were measured by autopsy on day 28. The results are shown FIG. 5.

As a result of measurement of tumor inhibitory effect, the tumor weight of the non-treatment group (negative control group) was on average 0.46±0.17 g, the tumor weight of the monolayer micelle composition (comparative example 3) treatment group was 0.37±0.09 g, and the tumor weight of the bilayer particle composition (inventive example 2) treatment group was 0.21±0.05 g. Therefore, the bilayer particle composition showed a tumor inhibitory effect of 55% or more compared with the monolayer micelle, and thus a very excellent tumor inhibitory effect.

Example 12: Pharmacokinetic Test in Beagle Dogs

The pharmacokinetic characteristics of the monolayer micelle composition (comparative example 3) were compared with those of the bilayer particle composition (inventive example 2) in beagle dogs. Male beagle dogs weighing 7-10 kg were divided into two groups, three dogs per each group, according to the body weight, and were intravenously administered with a composition comprising the monolayer micelle (comparative core-shell particle) of comparative example 2 and a bilayer particle composition (inventive example 2) at 0.5 mg/kg on the basis of SN-38 for 10 minutes infusion. Blood samples were taken at 0.33, 0.67, 1, 1.5, 2, 4, 8, 12, 24, 36 hours after the end of the administration, and the plasma obtained by centrifuging the blood was pretreated by the following method to measure the drug concentration in plasma. For sample pretreatment, 20 μL of S-(+)-camptothecin (500 ng/mL, dissolved in acetonitrile) as an internal standard substance was first added to 100 μL of plasma, and 500 μL of acetonitrile was further added, followed by vortex-mixing for 30 seconds. After the mixture was centrifuged at 12,000 rpm for 3 minutes, the supernatant was taken, and was injected 2 μL into an LC-MS/MS system (API-5,000 model, AB Sciex). Separation was carried out while the column was Gemini C18 (3 μm, 2.0×50 mm, Phenomenex, USA), the mobile phase was a 50% acetonitrile solution containing 0.1% formic acid, and the flow rate was 0.25 mL/min. MS/MS detection conditions were positive ion mode, and SN-38 glucuronide was detected at m/z 569.3→393.2, and the internal standard was detected at m/z 349.2→305.2.

Figure 6:
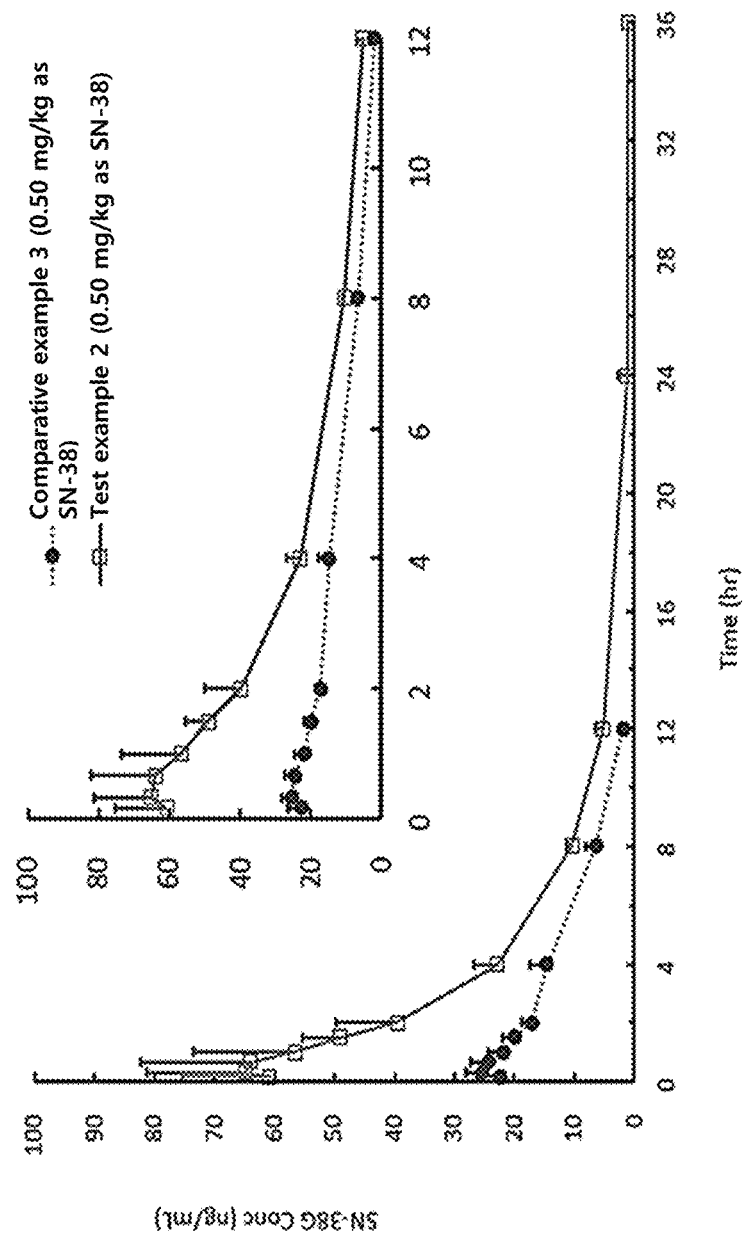
FIG. 6 is a graph showing the blood concentration of SN-38 Glucuronide for comparing pharmacokinetic characteristics between comparative core-shell particles (monolayer micelles) and inventive double core-shell particles (bilayer micelles).

The blood drug concentration over time after administration is shown in FIG. 6, and pharmacokinetic parameters therefor are shown in Table 9.

TABLE 9

Pharmacokinetic parameter comparison between monolayer micelle particle composition and bilayer particle composition

| No. | Micelle type | Dose (mg/kg) | Cmax (ng/mL) | Tmax (hr) | AUCt (ng · hr/mL) | Relative BA (%) |
|---|---|---|---|---|---|---|
| Comparative example 3 | Monolayer micelles | 0.5 | 25.30 ± 5.12 | 0.33 ± 0.00 | 131.84 ± 34.94 | — |
| Inventive example 2 | Double core-shell | 0.5 | 66.25 ± 16.34 | 0.44 ± 0.20 | 361.29 ± 96.25 | 275.6 |

*mean ± SD (n = 3)

In beagle dogs, SN-38 glucuronide produced directly from SN-38 solubilized in the particles of the embodiment was analyzed. The results confirmed that the bilayer particles of the embodiments of the present invention showed an increase in bioavailability by about 2.75 times, compared with the comparative monolayer micelles. It was determined from the above results that the inventive bilayer particles maximize the solubility of the poorly soluble drug SN-38 in vivo.

Although the present invention has been described in detail with reference to the specific features, it will be apparent to those skilled in the art that this description is only for a preferred embodiment and does not limit the scope of the present invention.

The invention claimed is:

1. A method for manufacturing a population of freeze-dried particles with particle size of less than 1 μm, said freeze-dried particles comprising
   (a) an inner core comprising
      (a1) a hydrophobic camptothecin compound; and
      (a2) a hydrophilic camptothecin compound; and
   (b) an outer shell surrounding the inner core, said outer shell being formed of an amphiphilic block copolymer,
   wherein the method comprises steps:
   (i) mixing the hydrophobic camptothecin compound (a1) and the hydrophilic camptothecin compound (a2) in an aqueous solvent;
   (ii) mixing the resulting mixture of step (i) with the amphiphilic block copolymer in an aqueous solvent to form particles comprising the inner core (a) and the outer shell (b); and
   (iii) freeze-drying the particles obtained in step (ii) to give the population of freeze-dried particles with particle size less than 1 μm,
   wherein the amphiphilic block copolymer comprises a hydrophobic block and a hydrophilic block in a same chain;
   wherein the hydrophobic camptothecin compound (a1) is selected from the group consisting of 7-ethyl-10-hydroxycamptothecin (SN-38), camptothecin, 10-hydroxycamptothecin, a pharmaceutical acceptable salt thereof, and a combination thereof;
   wherein the hydrophilic camptothecin compound (a2) is selected from irinotecan, topotecan, belotecan, exatecan, lurtotecan, sinotecan, rubitecan, 9-nitrocamptothecin, 9-aminocamptothecin, gimatecan, 7-t-butyldimethylsilyl-10-hydroxycamptothecin, diflomotecan, elomotecan, a pharmaceutically acceptable salt thereof, a glucuronide metabolite thereof, and a glucuronide metabolite of the hydrophobic camptothecin-based compound, and a combination thereof; and
   wherein a proportion of the freeze-dried particles with a size more than 200 nm in the population obtained in step (iii) is 11.8% or less as measured by dynamic light scattering (DLS) method.

2. The method of claim 1, wherein in step (i), the hydrophobic camptothecin compound (a1) is a basic aqueous solution of the hydrophobic camptothecin compound, said basic aqueous solution having a pH of 8-13.

3. The method of claim 2, wherein the basic aqueous solution of the hydrophobic camptothecin compound (a1) comprises a base selected from the group consisting of an inorganic alkali, an alkali salt of an organic acid, and an alkyl amine,
   wherein the inorganic alkali comprises sodium hydroxide, potassium hydroxide, sodium dihydrogenphosphate, potassium dihydrogenphosphate, magnesium hydroxide, sodium carbonate, sodium hydrogencarbonate, and a combination thereof.

4. The method of claim 1, wherein in step (i), the hydrophilic camptothecin (a2) is a neutral, basic, or acidic aqueous solution of the hydrophilic camptothecin.

5. The method of claim 4, wherein the acidic aqueous solution of the hydrophilic camptothecin (a2) comprises an inorganic acid selected from the group consisting of hydrochloric acid, nitric acid, sulfuric acid, and phosphoric acid; or an organic acid selected from the group consisting of citric acid, malic acid, lactic acid, acetic acid, and tartaric acid.

6. The method of claim 2, wherein step (i) further comprises (i-1) lowering a pH of the resulting mixture to 7 or lower.

7. The method of claim 6, wherein step (i) further comprises (i-2) subjecting the resulting mixture of pH 7 or lower to ultrasonication or vortexing.

8. The method of claim 1, wherein step (ii) mixing is carried out with ultrasonication or vortexing.

9. The method of claim 1, wherein the amphiphilic block copolymer comprises an A-B block or A-B-A block, wherein A is a hydrophilic segment formed from monomethoxy polyethylene glycol, dimethoxy polyethylene glycol, polyethylene glycol, polypropylene glycol, monomethoxy polypropylene glycol, polyethylene oxide, or polyacrylic acid; and wherein B is a hydrophobic segment formed from polylactic acid, polylactide, polyglycolic acid, polyglycolide, a polylactic acid-co-glycolic acid copolymer, polymandelic acid, polycaprolactone, polydioxan-2-one, polyglutamic acid, polyaspartic acid, polyornithine, or polyorthoester.

10. The method of claim 9, wherein a number average molecular weight of the hydrophilic segment A is 500-10,000 Da.

11. The method of claim 9, wherein a number average molecular weight of the hydrophobic segment B is 500-10,000 Da.

12. The method of claim 1, wherein a weight ratio of the hydrophobic camptothecin compound (a1) and the hydrophilic camptothecin compound (a2) is 1:10 to 10:1.

13. The method of claim 1, wherein a weight ratio of a total of the hydrophobic camptothecin compound (a1) plus the hydrophilic camptothecin compound (a2), and the amphiphilic block copolymer is 1:200 to 10:1.

14. The method of claim 1, wherein the number average particle size of the freeze-dried particles is 10-500 nm.

15. The method of claim 1, wherein the number average particle size of the freeze-dried particles is 20-200 nm.

16. The method of claim 1, wherein step (iii) freeze-drying the particles is carried out in the presence of a cryoprotectant.

17. The method of claim 16, wherein the cryoprotectant is mannitol or trehalose.

* * * * *